: US 9,283,374 B2
(45) Date of Patent: Mar. 15, 2016

(12) United States Patent
Hollett et al.

(54) DEVICES AND METHODS FOR DELIVERING ENERGY TO BODY LUMENS

(71) Applicant: Boston Scientific Scimed, Inc., Maple Grove, MN (US)

(72) Inventors: Andrew K. Hollett, Somerville, MA (US); Craig McGreevy, La Jolla, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 14/072,230

(22) Filed: Nov. 5, 2013

(65) Prior Publication Data

US 2014/0128949 A1     May 8, 2014

Related U.S. Application Data

(60) Provisional application No. 61/722,499, filed on Nov. 5, 2012.

(51) Int. Cl.
*A61N 1/05* (2006.01)
*A61B 18/14* (2006.01)
*A61B 18/00* (2006.01)

(52) U.S. Cl.
CPC .......... *A61N 1/0519* (2013.01); *A61B 18/1492* (2013.01); *A61B 2018/0016* (2013.01); *A61B 2018/00267* (2013.01); *A61B 2018/00541* (2013.01)

(58) Field of Classification Search
CPC ................... A61N 1/05; A61N 1/0519; A61B 2018/00267; A61B 2018/00541; A61B 18/1492
USPC ....................................................... 607/116
See application file for complete search history.

(56) References Cited

U.S. PATENT DOCUMENTS

| 612,724 A | 10/1898 | Hamilton |
| 1,155,169 A | 9/1915 | Starkweather |

(Continued)

FOREIGN PATENT DOCUMENTS

| DE | 19529634 A1 | 2/1997 |
| EP | 189329 A3 | 6/1987 |

(Continued)

OTHER PUBLICATIONS

International Search Report and Written Opinion for corresponding International Application No. PCT/US2013/068502, mailed Mar. 18, 2014, 13 pages.

(Continued)

*Primary Examiner* — Christopher A Flory
(74) *Attorney, Agent, or Firm* — Bookoff McAndrews, PLLC

(57) ABSTRACT

A medical device is disclosed for delivering energy to a body lumen. The device includes an elongate member including a proximal portion and a distal portion adapted for insertion into a body lumen; and an energy delivery device disposed adjacent the distal portion of the elongate member, the energy delivery device including at least one elongate electrode arm, wherein the elongate electrode arm is configured to transition between a first configuration and a second configuration different than the first configuration. The at least one elongate electrode arm includes an active region configured to contact and deliver energy to the body lumen. When the elongate electrode arm is in the first configuration, at least a portion of the active region of the elongate electrode arm extends radially inward toward a longitudinal axis of the energy delivery device.

19 Claims, 8 Drawing Sheets

(56) References Cited

U.S. PATENT DOCUMENTS

| | | | |
|---|---|---|---|
| 1,207,479 A | 12/1916 | Bisgaard |
| 1,216,183 A | 2/1917 | Swingle |
| 2,072,346 A | 3/1937 | Smith |
| 3,320,957 A | 5/1967 | Sokolik |
| 3,568,659 A | 3/1971 | Karnegis |
| 3,667,476 A | 6/1972 | Muller |
| 3,692,029 A | 9/1972 | Adair |
| 3,995,617 A | 12/1976 | Watkins et al. |
| 4,095,602 A | 6/1978 | Leveen |
| 4,116,589 A | 9/1978 | Rishton |
| 4,129,129 A | 12/1978 | Amrine |
| 4,154,246 A | 5/1979 | Leveen |
| 4,461,283 A | 7/1984 | Doi |
| 4,502,490 A | 3/1985 | Evans et al. |
| 4,503,855 A | 3/1985 | Maslanka |
| 4,512,762 A | 4/1985 | Spears |
| 4,522,212 A | 6/1985 | Gelinas et al. |
| 4,557,272 A | 12/1985 | Carr |
| 4,565,200 A | 1/1986 | Cosman |
| 4,567,882 A | 2/1986 | Heller |
| 4,584,998 A | 4/1986 | McGrail |
| 4,612,934 A | 9/1986 | Borkan |
| 4,621,642 A | 11/1986 | Chen |
| 4,621,882 A | 11/1986 | Krumme |
| 4,625,712 A | 12/1986 | Wampler |
| 4,643,186 A | 2/1987 | Rosen et al. |
| 4,646,737 A | 3/1987 | Hussein et al. |
| 4,674,497 A | 6/1987 | Ogasawara |
| 4,683,890 A | 8/1987 | Hewson |
| 4,704,121 A | 11/1987 | Moise |
| 4,706,688 A | 11/1987 | Don Michael et al. |
| 4,709,698 A | 12/1987 | Johnston et al. |
| 4,739,759 A | 4/1988 | Rexroth et al. |
| 4,754,065 A | 6/1988 | Levenson et al. |
| 4,754,752 A | 7/1988 | Ginsburg et al. |
| 4,765,959 A | 8/1988 | Fukasawa |
| 4,772,112 A | 9/1988 | Zider et al. |
| 4,773,899 A | 9/1988 | Spears |
| 4,779,614 A | 10/1988 | Moise |
| 4,784,135 A | 11/1988 | Blum et al. |
| 4,790,305 A | 12/1988 | Zoltan et al. |
| 4,799,479 A | 1/1989 | Spears |
| 4,802,492 A | 2/1989 | Grunstein |
| 4,817,586 A | 4/1989 | Wampler |
| 4,825,871 A | 5/1989 | Cansell |
| 4,827,935 A | 5/1989 | Geddes et al. |
| 4,846,152 A | 7/1989 | Wampler et al. |
| 4,862,886 A | 9/1989 | Clarke et al. |
| 4,895,557 A | 1/1990 | Moise et al. |
| 4,906,229 A | 3/1990 | Wampler |
| 4,907,589 A | 3/1990 | Cosman |
| 4,908,012 A | 3/1990 | Moise et al. |
| 4,920,978 A | 5/1990 | Colvin |
| 4,944,722 A | 7/1990 | Carriker et al. |
| 4,955,377 A | 9/1990 | Lennox et al. |
| 4,967,765 A | 11/1990 | Turner et al. |
| 4,969,865 A | 11/1990 | Hwang et al. |
| 4,976,709 A | 12/1990 | Sand |
| 4,985,014 A | 1/1991 | Orejola |
| 4,991,603 A | 2/1991 | Cohen et al. |
| 5,009,636 A | 4/1991 | Wortley et al. |
| 5,009,936 A | 4/1991 | Yamanaka et al. |
| 5,010,892 A | 4/1991 | Colvin et al. |
| 5,019,075 A | 5/1991 | Spears et al. |
| 5,027,829 A | 7/1991 | Larsen |
| 5,030,645 A | 7/1991 | Kollonitsch |
| 5,036,848 A | 8/1991 | Hewson |
| 5,053,033 A | 10/1991 | Clarke |
| 5,056,519 A | 10/1991 | Vince |
| 5,074,860 A | 12/1991 | Gregory et al. |
| 5,078,716 A | 1/1992 | Doll |
| 5,084,044 A | 1/1992 | Quint |
| 5,096,916 A | 3/1992 | Skupin |
| 5,100,388 A | 3/1992 | Behl et al. |
| 5,100,423 A | 3/1992 | Fearnot |
| 5,103,804 A | 4/1992 | Abele et al. |
| 5,105,826 A | 4/1992 | Smits et al. |
| 5,106,360 A | 4/1992 | Ishiwara et al. |
| 5,107,830 A | 4/1992 | Younes |
| 5,114,423 A | 5/1992 | Kasprzyk et al. |
| 5,116,864 A | 5/1992 | March et al. |
| 5,117,828 A | 6/1992 | Metzger et al. |
| 5,135,517 A | 8/1992 | McCoy |
| 5,152,286 A | 10/1992 | Sitko et al. |
| 5,165,420 A | 11/1992 | Strickland |
| 5,167,223 A | 12/1992 | Koros et al. |
| 5,170,803 A | 12/1992 | Hewson et al. |
| 5,174,288 A | 12/1992 | Bardy et al. |
| 5,188,602 A | 2/1993 | Nichols |
| 5,191,883 A | 3/1993 | Lennox et al. |
| 5,213,576 A | 5/1993 | Abiuso et al. |
| 5,215,103 A | 6/1993 | Desai |
| 5,231,996 A | 8/1993 | Bardy et al. |
| 5,232,444 A | 8/1993 | Just et al. |
| 5,234,456 A | 8/1993 | Silvestrini |
| 5,254,088 A | 10/1993 | Lundquist et al. |
| 5,255,678 A | 10/1993 | Deslauriers et al. |
| 5,255,679 A | 10/1993 | Imran |
| 5,265,604 A | 11/1993 | Vince |
| 5,269,758 A | 12/1993 | Taheri |
| 5,281,218 A | 1/1994 | Imran |
| 5,292,331 A | 3/1994 | Boneau |
| 5,293,869 A | 3/1994 | Edwards et al. |
| 5,309,910 A | 5/1994 | Edwards et al. |
| 5,311,866 A | 5/1994 | Kagan et al. |
| 5,313,943 A | 5/1994 | Houser et al. |
| 5,324,284 A | 6/1994 | Imran |
| 5,343,936 A | 9/1994 | Beatenbough et al. |
| 5,345,936 A | 9/1994 | Pomeranz et al. |
| 5,366,443 A | 11/1994 | Eggers et al. |
| 5,368,591 A | 11/1994 | Lennox et al. |
| 5,370,644 A | 12/1994 | Langberg |
| 5,370,679 A | 12/1994 | Atlee, III |
| 5,374,287 A | 12/1994 | Rubin |
| 5,383,917 A | 1/1995 | Desai et al. |
| 5,393,207 A | 2/1995 | Maher et al. |
| 5,394,880 A | 3/1995 | Atlee, III |
| 5,396,887 A | 3/1995 | Imran |
| 5,400,778 A | 3/1995 | Jonson et al. |
| 5,400,783 A | 3/1995 | Pomeranz et al. |
| 5,411,025 A | 5/1995 | Webster |
| 5,415,166 A | 5/1995 | Imran |
| 5,415,656 A | 5/1995 | Tihon et al. |
| 5,417,687 A | 5/1995 | Nardella et al. |
| 5,422,362 A | 6/1995 | Vincent et al. |
| 5,423,744 A | 6/1995 | Gencheff et al. |
| 5,423,811 A | 6/1995 | Imran et al. |
| 5,425,023 A | 6/1995 | Haraguchi et al. |
| 5,425,703 A | 6/1995 | Feiring |
| 5,425,811 A | 6/1995 | Mashita |
| 5,431,696 A | 7/1995 | Atlee, III |
| 5,433,730 A | 7/1995 | Alt |
| 5,437,665 A | 8/1995 | Munro |
| 5,443,470 A | 8/1995 | Stern et al. |
| 5,454,782 A | 10/1995 | Perkins |
| 5,456,667 A | 10/1995 | Ham et al. |
| 5,458,596 A | 10/1995 | Lax et al. |
| 5,465,717 A | 11/1995 | Imran et al. |
| 5,471,982 A | 12/1995 | Edwards et al. |
| 5,474,530 A | 12/1995 | Passafaro et al. |
| 5,478,309 A | 12/1995 | Sweezer et al. |
| 5,496,271 A | 3/1996 | Burton et al. |
| 5,496,311 A | 3/1996 | Abele et al. |
| 5,496,312 A | 3/1996 | Klicek |
| 5,500,011 A | 3/1996 | Desai |
| 5,505,728 A | 4/1996 | Ellman et al. |
| 5,505,730 A | 4/1996 | Edwards |
| 5,507,791 A | 4/1996 | Sit'ko |
| 5,509,419 A | 4/1996 | Edwards et al. |
| 5,522,862 A | 6/1996 | Testerman et al. |
| 5,531,779 A | 7/1996 | Dahl et al. |
| 5,540,681 A | 7/1996 | Strul et al. |
| 5,545,161 A | 8/1996 | Imran |
| 5,545,193 A | 8/1996 | Fleischman et al. |

(56) References Cited

U.S. PATENT DOCUMENTS

| | | | |
|---|---|---|---|
| 5,547,469 | A | 8/1996 | Rowland et al. |
| 5,549,559 | A | 8/1996 | Eshel |
| 5,549,655 | A | 8/1996 | Erickson |
| 5,549,661 | A | 8/1996 | Kordis et al. |
| RE35,330 | E | 9/1996 | Malone et al. |
| 5,558,073 | A | 9/1996 | Pomeranz et al. |
| 5,562,608 | A | 10/1996 | Sekins et al. |
| 5,571,074 | A | 11/1996 | Buckman et al. |
| 5,571,088 | A | 11/1996 | Lennox et al. |
| 5,574,059 | A | 11/1996 | Regunathan et al. |
| 5,575,810 | A | 11/1996 | Swanson et al. |
| 5,578,072 | A | 11/1996 | Barone et al. |
| 5,582,609 | A | 12/1996 | Swanson et al. |
| 5,588,432 | A | 12/1996 | Crowley |
| 5,588,812 | A | 12/1996 | Taylor et al. |
| 5,595,183 | A | 1/1997 | Swanson et al. |
| 5,598,848 | A | 2/1997 | Swanson et al. |
| 5,599,345 | A | 2/1997 | Edwards et al. |
| 5,601,088 | A | 2/1997 | Swanson et al. |
| 5,605,157 | A | 2/1997 | Panescu et al. |
| 5,607,419 | A | 3/1997 | Amplatz et al. |
| 5,607,462 | A | 3/1997 | Imran |
| 5,620,438 | A | 4/1997 | Amplatz et al. |
| 5,623,940 | A | 4/1997 | Daikuzono |
| 5,624,439 | A | 4/1997 | Edwards et al. |
| 5,626,618 | A | 5/1997 | Ward et al. |
| 5,630,425 | A | 5/1997 | Panescu et al. |
| 5,630,794 | A | 5/1997 | Lax et al. |
| 5,634,471 | A | 6/1997 | Fairfax et al. |
| 5,641,326 | A | 6/1997 | Adams |
| 5,647,870 | A | 7/1997 | Kordis et al. |
| 5,660,175 | A | 8/1997 | Dayal |
| 5,678,535 | A | 10/1997 | DiMarco |
| 5,680,860 | A | 10/1997 | Imran |
| 5,681,280 | A | 10/1997 | Rusk et al. |
| 5,681,308 | A | 10/1997 | Edwards et al. |
| 5,687,723 | A | 11/1997 | Avitall |
| 5,688,267 | A | 11/1997 | Panescu et al. |
| 5,693,078 | A | 12/1997 | Desai et al. |
| 5,694,934 | A | 12/1997 | Edelman |
| 5,695,471 | A | 12/1997 | Wampler |
| 5,699,799 | A | 12/1997 | Xu et al. |
| 5,702,386 | A | 12/1997 | Stern et al. |
| 5,707,218 | A | 1/1998 | Maher et al. |
| 5,707,336 | A | 1/1998 | Rubin |
| 5,707,352 | A | 1/1998 | Sekins et al. |
| 5,722,401 | A | 3/1998 | Pietroski et al. |
| 5,722,403 | A | 3/1998 | McGee et al. |
| 5,722,416 | A | 3/1998 | Swanson et al. |
| 5,725,525 | A | 3/1998 | Kordis |
| 5,727,569 | A | 3/1998 | Benetti et al. |
| 5,728,094 | A | 3/1998 | Edwards |
| 5,730,128 | A | 3/1998 | Pomeranz et al. |
| 5,730,704 | A | 3/1998 | Avitall |
| 5,730,726 | A | 3/1998 | Klingenstein |
| 5,730,741 | A | 3/1998 | Horzewski et al. |
| 5,735,846 | A | 4/1998 | Panescu et al. |
| 5,740,808 | A | 4/1998 | Panescu et al. |
| 5,741,248 | A | 4/1998 | Stern et al. |
| 5,752,518 | A | 5/1998 | McGee et al. |
| 5,755,714 | A | 5/1998 | Murphy-Chutorian |
| 5,755,715 | A | 5/1998 | Stern et al. |
| 5,755,753 | A | 5/1998 | Knowlton |
| 5,759,158 | A | 6/1998 | Swanson |
| 5,765,568 | A | 6/1998 | Sweezer et al. |
| 5,769,846 | A | 6/1998 | Edwards et al. |
| 5,772,590 | A | 6/1998 | Webster |
| 5,779,669 | A | 7/1998 | Haissaguerre et al. |
| 5,779,698 | A | 7/1998 | Clayman et al. |
| 5,782,239 | A | 7/1998 | Webster |
| 5,782,797 | A | 7/1998 | Schweich et al. |
| 5,782,827 | A | 7/1998 | Gough et al. |
| 5,782,848 | A | 7/1998 | Lennox |
| 5,782,899 | A | 7/1998 | Imran |
| 5,792,064 | A | 8/1998 | Panescu et al. |
| 5,795,303 | A | 8/1998 | Swanson et al. |
| 5,800,375 | A | 9/1998 | Sweezer et al. |
| 5,807,306 | A | 9/1998 | Shapland et al. |
| 5,810,757 | A | 9/1998 | Sweezer et al. |
| 5,810,807 | A | 9/1998 | Ganz et al. |
| 5,817,028 | A | 10/1998 | Anderson |
| 5,817,073 | A | 10/1998 | Krespi |
| 5,820,554 | A | 10/1998 | Davis et al. |
| 5,823,189 | A | 10/1998 | Kordis |
| 5,827,277 | A | 10/1998 | Edwards |
| 5,833,651 | A | 11/1998 | Donovan et al. |
| 5,836,905 | A | 11/1998 | Lemelson et al. |
| 5,836,947 | A | 11/1998 | Fleischman et al. |
| 5,837,001 | A | 11/1998 | Mackey |
| 5,843,075 | A | 12/1998 | Taylor |
| 5,843,077 | A | 12/1998 | Edwards |
| 5,846,238 | A | 12/1998 | Jackson et al. |
| 5,848,969 | A | 12/1998 | Panescu et al. |
| 5,848,972 | A | 12/1998 | Triedman et al. |
| 5,849,026 | A | 12/1998 | Zhou et al. |
| 5,855,577 | A | 1/1999 | Murphy-Chutorian et al. |
| 5,860,974 | A | 1/1999 | Abele |
| 5,863,291 | A | 1/1999 | Schaer |
| 5,865,791 | A | 2/1999 | Whayne et al. |
| 5,868,740 | A | 2/1999 | Leveen et al. |
| 5,871,443 | A | 2/1999 | Edwards et al. |
| 5,871,523 | A | 2/1999 | Fleischman et al. |
| 5,873,852 | A | 2/1999 | Vigil et al. |
| 5,873,865 | A | 2/1999 | Horzewski et al. |
| 5,876,340 | A | 3/1999 | Tu et al. |
| 5,876,399 | A | 3/1999 | Chia et al. |
| 5,881,727 | A | 3/1999 | Edwards |
| 5,882,346 | A | 3/1999 | Pomeranz et al. |
| 5,891,135 | A | 4/1999 | Jackson et al. |
| 5,891,136 | A | 4/1999 | McGee et al. |
| 5,891,138 | A | 4/1999 | Tu et al. |
| 5,893,847 | A | 4/1999 | Kordis |
| 5,897,554 | A | 4/1999 | Chia et al. |
| 5,899,882 | A | 5/1999 | Waksman et al. |
| 5,904,651 | A | 5/1999 | Swanson et al. |
| 5,904,680 | A * | 5/1999 | Kordis et al. .......... 606/41 |
| 5,904,711 | A | 5/1999 | Flom et al. |
| 5,906,636 | A | 5/1999 | Casscells, III et al. |
| 5,908,445 | A | 6/1999 | Whayne et al. |
| 5,908,446 | A | 6/1999 | Imran |
| 5,908,839 | A | 6/1999 | Levitt et al. |
| 5,911,218 | A | 6/1999 | DiMarco |
| 5,916,235 | A | 6/1999 | Guglielmi |
| 5,919,147 | A | 7/1999 | Jain |
| 5,919,172 | A | 7/1999 | Golba |
| 5,924,424 | A | 7/1999 | Stevens et al. |
| 5,928,228 | A | 7/1999 | Kordis et al. |
| 5,931,835 | A | 8/1999 | Mackey |
| 5,935,079 | A | 8/1999 | Swanson et al. |
| 5,941,869 | A | 8/1999 | Patterson et al. |
| 5,951,494 | A | 9/1999 | Wang et al. |
| 5,951,546 | A | 9/1999 | Lorentzen |
| 5,954,661 | A | 9/1999 | Greenspon et al. |
| 5,954,662 | A | 9/1999 | Swanson et al. |
| 5,954,717 | A | 9/1999 | Behl et al. |
| 5,957,961 | A | 9/1999 | Maguire et al. |
| 5,964,753 | A | 10/1999 | Edwards |
| 5,964,796 | A | 10/1999 | Imran |
| 5,971,983 | A | 10/1999 | Lesh |
| 5,972,026 | A | 10/1999 | Laufer et al. |
| 5,976,175 | A | 11/1999 | Hirano et al. |
| 5,976,709 | A | 11/1999 | Kageyama et al. |
| 5,979,456 | A | 11/1999 | Magovern |
| 5,980,563 | A | 11/1999 | Tu et al. |
| 5,984,917 | A | 11/1999 | Fleischman et al. |
| 5,984,971 | A | 11/1999 | Faccioli et al. |
| 5,991,650 | A | 11/1999 | Swanson et al. |
| 5,992,419 | A | 11/1999 | Sterzer et al. |
| 5,993,462 | A | 11/1999 | Pomeranz et al. |
| 5,997,534 | A | 12/1999 | Tu et al. |
| 5,999,855 | A | 12/1999 | DiMarco |
| 6,001,054 | A | 12/1999 | Regulla et al. |
| 6,003,517 | A | 12/1999 | Sheffield et al. |
| 6,004,269 | A | 12/1999 | Crowley et al. |

(56) References Cited

U.S. PATENT DOCUMENTS

| | | |
|---|---|---|
| 6,006,755 A | 12/1999 | Edwards |
| 6,008,211 A | 12/1999 | Robinson et al. |
| 6,009,877 A | 1/2000 | Edwards |
| 6,010,500 A | 1/2000 | Sherman et al. |
| 6,014,579 A | 1/2000 | Pomeranz et al. |
| 6,016,437 A | 1/2000 | Tu et al. |
| 6,023,638 A | 2/2000 | Swanson |
| 6,024,740 A | 2/2000 | Lesh et al. |
| 6,029,091 A | 2/2000 | De La Rama et al. |
| 6,033,397 A | 3/2000 | Laufer et al. |
| 6,036,687 A | 3/2000 | Laufer et al. |
| 6,036,689 A | 3/2000 | Tu et al. |
| 6,039,731 A | 3/2000 | Taylor et al. |
| 6,042,580 A | 3/2000 | Simpson |
| 6,045,549 A | 4/2000 | Smethers et al. |
| 6,045,550 A | 4/2000 | Simpson et al. |
| 6,050,992 A | 4/2000 | Nichols |
| 6,053,172 A | 4/2000 | Hovda et al. |
| 6,053,909 A | 4/2000 | Shadduck |
| 6,056,744 A | 5/2000 | Edwards |
| 6,056,769 A | 5/2000 | Epstein et al. |
| 6,063,078 A | 5/2000 | Wittkampf |
| 6,071,280 A | 6/2000 | Edwards et al. |
| 6,071,281 A | 6/2000 | Burnside et al. |
| 6,071,282 A | 6/2000 | Fleischman |
| 6,083,255 A | 7/2000 | Laufer et al. |
| 6,090,104 A | 7/2000 | Webster |
| 6,092,528 A | 7/2000 | Edwards |
| 6,102,886 A | 8/2000 | Lundquist et al. |
| 6,106,522 A | 8/2000 | Fleischman et al. |
| 6,106,524 A | 8/2000 | Eggers et al. |
| 6,123,702 A | 9/2000 | Swanson et al. |
| 6,123,703 A | 9/2000 | Tu et al. |
| 6,129,725 A | 10/2000 | Tu et al. |
| 6,139,527 A | 10/2000 | Laufer et al. |
| 6,139,571 A | 10/2000 | Fuller et al. |
| 6,142,993 A | 11/2000 | Whayne et al. |
| 6,143,013 A | 11/2000 | Samson et al. |
| 6,149,647 A | 11/2000 | Tu et al. |
| 6,152,143 A | 11/2000 | Edwards |
| 6,152,899 A * | 11/2000 | Farley et al. .................. 604/113 |
| 6,159,194 A | 12/2000 | Eggers et al. |
| 6,179,833 B1 | 1/2001 | Taylor |
| 6,183,468 B1 | 2/2001 | Swanson et al. |
| 6,198,970 B1 | 3/2001 | Freed et al. |
| 6,200,311 B1 | 3/2001 | Danek et al. |
| 6,200,332 B1 | 3/2001 | Del Giglio |
| 6,200,333 B1 | 3/2001 | Laufer |
| 6,210,367 B1 | 4/2001 | Carr |
| 6,212,433 B1 | 4/2001 | Behl |
| 6,214,002 B1 | 4/2001 | Fleischman et al. |
| 6,216,043 B1 | 4/2001 | Swanson et al. |
| 6,216,044 B1 | 4/2001 | Kordis |
| 6,217,576 B1 | 4/2001 | Tu et al. |
| 6,235,024 B1 | 5/2001 | Tu |
| 6,241,727 B1 | 6/2001 | Tu et al. |
| 6,245,065 B1 | 6/2001 | Panescu et al. |
| 6,254,598 B1 | 7/2001 | Edwards et al. |
| 6,258,087 B1 | 7/2001 | Edwards et al. |
| 6,264,653 B1 | 7/2001 | Falwell |
| 6,269,813 B1 | 8/2001 | Fitzgerald et al. |
| 6,270,476 B1 | 8/2001 | Santoianni et al. |
| 6,273,907 B1 | 8/2001 | Laufer |
| 6,283,988 B1 | 9/2001 | Laufer et al. |
| 6,283,989 B1 | 9/2001 | Laufer et al. |
| 6,287,304 B1 | 9/2001 | Eggers et al. |
| 6,296,639 B1 | 10/2001 | Truckai et al. |
| 6,319,251 B1 | 11/2001 | Tu et al. |
| 6,322,559 B1 | 11/2001 | Daulton et al. |
| 6,322,584 B2 | 11/2001 | Ingle et al. |
| 6,338,727 B1 | 1/2002 | Noda et al. |
| 6,338,836 B1 | 1/2002 | Kuth et al. |
| 6,346,104 B2 | 2/2002 | Daly et al. |
| 6,355,031 B1 | 3/2002 | Edwards et al. |
| 6,379,352 B1 | 4/2002 | Reynolds et al. |
| 6,409,723 B1 | 6/2002 | Edwards |
| 6,411,852 B1 * | 6/2002 | Danek et al. .................. 607/42 |
| 6,416,511 B1 | 7/2002 | Lesh et al. |
| 6,416,740 B1 | 7/2002 | Unger |
| 6,423,105 B1 | 7/2002 | Iijima et al. |
| 6,425,895 B1 | 7/2002 | Swanson et al. |
| 6,440,129 B1 | 8/2002 | Simpson |
| 6,442,435 B2 | 8/2002 | King et al. |
| 6,458,121 B1 | 10/2002 | Rosenstock et al. |
| 6,460,545 B2 | 10/2002 | Kordis |
| 6,488,673 B1 | 12/2002 | Laufer et al. |
| 6,488,679 B1 | 12/2002 | Swanson et al. |
| 6,493,589 B1 | 12/2002 | Medhkour et al. |
| 6,494,880 B1 | 12/2002 | Swanson et al. |
| 6,496,738 B2 | 12/2002 | Carr |
| 6,514,246 B1 | 2/2003 | Swanson et al. |
| 6,526,320 B2 | 2/2003 | Mitchell |
| 6,529,756 B1 | 3/2003 | Phan et al. |
| 6,544,226 B1 | 4/2003 | Gaiser et al. |
| 6,544,262 B2 | 4/2003 | Fleischman |
| 6,547,788 B1 | 4/2003 | Maguire et al. |
| 6,558,378 B2 | 5/2003 | Sherman et al. |
| 6,572,612 B2 | 6/2003 | Stewart et al. |
| 6,575,623 B2 | 6/2003 | Werneth |
| 6,575,969 B1 | 6/2003 | Rittman, III et al. |
| 6,582,427 B1 | 6/2003 | Goble et al. |
| 6,582,430 B2 | 6/2003 | Hall |
| 6,589,235 B2 | 7/2003 | Wong et al. |
| 6,610,054 B1 | 8/2003 | Edwards et al. |
| 6,620,159 B2 | 9/2003 | Hegde |
| 6,626,903 B2 | 9/2003 | McGuckin et al. |
| 6,634,363 B1 | 10/2003 | Danek et al. |
| 6,635,056 B2 | 10/2003 | Kadhiresan et al. |
| 6,638,273 B1 * | 10/2003 | Farley et al. .................. 606/27 |
| 6,640,120 B1 | 10/2003 | Swanson et al. |
| 6,645,200 B1 | 11/2003 | Koblish et al. |
| 6,652,548 B2 | 11/2003 | Evans et al. |
| 6,669,687 B1 | 12/2003 | Saadat |
| 6,669,693 B2 | 12/2003 | Friedman |
| 6,673,068 B1 | 1/2004 | Berube |
| 6,692,492 B2 | 2/2004 | Simpson et al. |
| 6,699,243 B2 | 3/2004 | West et al. |
| 6,714,822 B2 | 3/2004 | King et al. |
| 6,723,091 B2 | 4/2004 | Goble et al. |
| 6,743,197 B1 | 6/2004 | Edwards |
| 6,749,604 B1 | 6/2004 | Eggers et al. |
| 6,749,606 B2 | 6/2004 | Keast et al. |
| 6,767,347 B2 | 7/2004 | Sharkey et al. |
| 6,770,070 B1 | 8/2004 | Balbierz |
| 6,802,843 B2 | 10/2004 | Truckai et al. |
| 6,805,131 B2 | 10/2004 | Kordis |
| 6,837,888 B2 | 1/2005 | Ciarrocca et al. |
| 6,840,243 B2 | 1/2005 | Deem et al. |
| 6,849,073 B2 | 2/2005 | Hoey et al. |
| 6,852,091 B2 | 2/2005 | Edwards et al. |
| 6,852,110 B2 | 2/2005 | Roy et al. |
| 6,866,662 B2 | 3/2005 | Fuimaono et al. |
| 6,881,213 B2 | 4/2005 | Ryan et al. |
| 6,893,436 B2 | 5/2005 | Woodard et al. |
| 6,893,439 B2 | 5/2005 | Fleischman |
| 6,895,267 B2 | 5/2005 | Panescu et al. |
| 6,904,303 B2 | 6/2005 | Phan et al. |
| 6,917,834 B2 | 7/2005 | Koblish et al. |
| 6,939,346 B2 | 9/2005 | Kannenberg et al. |
| 6,954,977 B2 | 10/2005 | Maguire et al. |
| 7,027,869 B2 | 4/2006 | Danek et al. |
| 7,043,307 B1 | 5/2006 | Zelickson et al. |
| 7,104,987 B2 | 9/2006 | Biggs et al. |
| 7,104,990 B2 | 9/2006 | Jenkins et al. |
| 7,118,568 B2 | 10/2006 | Hassett et al. |
| 7,122,033 B2 | 10/2006 | Wood |
| 7,131,445 B2 | 11/2006 | Amoah |
| 7,186,251 B2 | 3/2007 | Malecki et al. |
| 7,198,635 B2 | 4/2007 | Danek et al. |
| 7,200,445 B1 | 4/2007 | Dalbec et al. |
| 7,241,295 B2 | 7/2007 | Maguire |
| 7,255,693 B1 | 8/2007 | Johnston et al. |
| 7,264,002 B2 | 9/2007 | Danek et al. |
| 7,266,414 B2 | 9/2007 | Cornelius et al. |

(56) References Cited

U.S. PATENT DOCUMENTS

| | | |
|---|---|---|
| 7,273,055 B2 | 9/2007 | Danek et al. |
| 7,425,212 B1 | 9/2008 | Danek et al. |
| 7,542,802 B2 | 6/2009 | Biggs et al. |
| 7,556,624 B2 | 7/2009 | Laufer et al. |
| 7,740,017 B2 | 6/2010 | Danek et al. |
| 8,161,978 B2 | 4/2012 | Danek et al. |
| 8,465,486 B2 | 6/2013 | Danek et al. |
| 8,584,681 B2 | 11/2013 | Danek et al. |
| 2002/0091379 A1* | 7/2002 | Danek et al. .................. 606/32 |
| 2002/0133150 A1* | 9/2002 | Whayne et al. ................ 606/41 |
| 2002/0161422 A1* | 10/2002 | Swanson et al. ............. 607/119 |
| 2003/0023287 A1* | 1/2003 | Edwards et al. ............. 607/101 |
| 2003/0050631 A1 | 3/2003 | Mody et al. |
| 2003/0060820 A1 | 3/2003 | Maguire et al. |
| 2003/0065371 A1 | 4/2003 | Satake |
| 2003/0069570 A1 | 4/2003 | Witzel et al. |
| 2003/0074039 A1* | 4/2003 | Puskas ......................... 607/118 |
| 2003/0187430 A1 | 10/2003 | Vorisek |
| 2003/0236455 A1 | 12/2003 | Swanson et al. |
| 2004/0153056 A1 | 8/2004 | Muller et al. |
| 2004/0249401 A1 | 12/2004 | Rabiner et al. |
| 2005/0010270 A1 | 1/2005 | Laufer |
| 2005/0096644 A1 | 5/2005 | Hall et al. |
| 2005/0165391 A1* | 7/2005 | Maguire et al. ................ 606/41 |
| 2005/0171396 A1 | 8/2005 | Pankratov et al. |
| 2005/0193279 A1 | 9/2005 | Daners |
| 2005/0203503 A1 | 9/2005 | Edwards et al. |
| 2005/0240176 A1 | 10/2005 | Oral et al. |
| 2005/0251128 A1 | 11/2005 | Amoah |
| 2006/0062808 A1 | 3/2006 | Laufer et al. |
| 2006/0079887 A1 | 4/2006 | Buysse et al. |
| 2006/0089637 A1 | 4/2006 | Werneth et al. |
| 2006/0135953 A1 | 6/2006 | Kania et al. |
| 2006/0137698 A1 | 6/2006 | Danek et al. |
| 2006/0189975 A1* | 8/2006 | Whayne et al. ................ 606/41 |
| 2006/0247617 A1 | 11/2006 | Danek et al. |
| 2006/0247618 A1 | 11/2006 | Kaplan et al. |
| 2006/0247619 A1 | 11/2006 | Kaplan et al. |
| 2006/0247726 A1 | 11/2006 | Biggs et al. |
| 2006/0247727 A1 | 11/2006 | Biggs et al. |
| 2006/0247746 A1 | 11/2006 | Danek et al. |
| 2006/0254600 A1 | 11/2006 | Danek et al. |
| 2006/0278243 A1 | 12/2006 | Danek et al. |
| 2006/0278244 A1 | 12/2006 | Danek et al. |
| 2006/0282071 A1 | 12/2006 | Utley et al. |
| 2007/0074719 A1 | 4/2007 | Danek et al. |
| 2007/0083194 A1 | 4/2007 | Kunis et al. |
| 2007/0083197 A1 | 4/2007 | Danek et al. |
| 2007/0102011 A1 | 5/2007 | Danek et al. |
| 2007/0106292 A1 | 5/2007 | Kaplan et al. |
| 2007/0106296 A1 | 5/2007 | Laufer et al. |
| 2007/0106348 A1 | 5/2007 | Laufer |
| 2007/0118184 A1 | 5/2007 | Danek et al. |
| 2007/0118190 A1 | 5/2007 | Danek et al. |
| 2007/0123958 A1 | 5/2007 | Laufer |
| 2007/0123961 A1 | 5/2007 | Danek et al. |
| 2007/0129720 A1 | 6/2007 | Demarais et al. |
| 2008/0004596 A1 | 1/2008 | Yun et al. |
| 2008/0097424 A1 | 4/2008 | Wizeman et al. |
| 2008/0255642 A1 | 10/2008 | Zarins et al. |
| 2008/0312725 A1* | 12/2008 | Penner ......................... 607/119 |
| 2009/0018538 A1 | 1/2009 | Webster et al. |
| 2009/0030477 A1 | 1/2009 | Jarrard |
| 2009/0043301 A1 | 2/2009 | Jarrard et al. |
| 2009/0069797 A1 | 3/2009 | Danek et al. |
| 2009/0112203 A1 | 4/2009 | Danek et al. |
| 2009/0143705 A1 | 6/2009 | Danek et al. |
| 2009/0143776 A1 | 6/2009 | Danek et al. |
| 2009/0192505 A1 | 7/2009 | Askew et al. |
| 2009/0192508 A1 | 7/2009 | Laufer et al. |
| 2009/0248005 A1 | 10/2009 | Rusin et al. |
| 2009/0254079 A1* | 10/2009 | Edwards et al. ................ 606/33 |
| 2009/0306644 A1 | 12/2009 | Mayse et al. |
| 2010/0094376 A1* | 4/2010 | Penner ........................... 607/42 |
| 2010/0160906 A1 | 6/2010 | Jarrard |
| 2011/0166569 A1* | 7/2011 | Whayne et al. ................ 606/41 |
| 2012/0157985 A1 | 6/2012 | Ballou et al. |
| 2012/0215278 A1* | 8/2012 | Penner ........................... 607/42 |
| 2012/0271139 A1* | 10/2012 | Kordis et al. ................ 600/375 |
| 2014/0018788 A1* | 1/2014 | Engelman et al. .............. 606/33 |
| 2014/0128936 A1* | 5/2014 | Laufer et al. ................... 607/42 |
| 2014/0180306 A1* | 6/2014 | Grubac et al. ............... 606/129 |
| 2015/0080693 A1* | 3/2015 | Solis ............................. 600/374 |

FOREIGN PATENT DOCUMENTS

| | | |
|---|---|---|
| EP | 286145 A2 | 10/1988 |
| EP | 280225 A3 | 3/1989 |
| EP | 286145 A3 | 10/1990 |
| EP | 282225 B1 | 6/1992 |
| EP | 908713 A1 | 4/1999 |
| EP | 908150 B1 | 5/2003 |
| EP | 768091 B1 | 7/2003 |
| EP | 1297795 B1 | 8/2005 |
| FR | 2659240 B1 | 7/1997 |
| GB | 2233293 A | 1/1991 |
| GB | 2233293 B | 2/1994 |
| JP | 59167707 A2 | 9/1984 |
| JP | 7289557 A | 11/1995 |
| JP | 9047518 A2 | 2/1997 |
| JP | 9243837 A2 | 9/1997 |
| JP | 10026709 A2 | 1/1998 |
| RU | 2053814 C1 | 2/1996 |
| RU | 2091054 C1 | 9/1997 |
| SU | 545358 T | 2/1977 |
| WO | WO-8911311 A1 | 11/1989 |
| WO | WO-9304734 A1 | 3/1993 |
| WO | WO 94/12098 | 6/1994 |
| WO | WO 95/01751 | 1/1995 |
| WO | WO-9502370 A3 | 3/1995 |
| WO | WO-9510322 A1 | 4/1995 |
| WO | WO-9604860 A1 | 2/1996 |
| WO | WO-9610961 A1 | 4/1996 |
| WO | WO 97/17905 A1 | 5/1997 |
| WO | WO-9732532 A1 | 9/1997 |
| WO | WO-9733715 A1 | 9/1997 |
| WO | WO-9737715 A1 | 10/1997 |
| WO | WO-9740751 A1 | 11/1997 |
| WO | WO-9844854 A1 | 10/1998 |
| WO | WO-9852480 A1 | 11/1998 |
| WO | WO-9856234 A1 | 12/1998 |
| WO | WO-9856324 A1 | 12/1998 |
| WO | WO 99/03413 A1 | 1/1999 |
| WO | WO-9858681 A3 | 3/1999 |
| WO | WO-9913779 A2 | 3/1999 |
| WO | WO-9932040 A1 | 7/1999 |
| WO | WO-9934741 A1 | 7/1999 |
| WO | WO-9944506 A1 | 9/1999 |
| WO | WO-9945855 A1 | 9/1999 |
| WO | WO-9964109 A1 | 12/1999 |
| WO | WO 00/51513 | 9/2000 |
| WO | WO-0051510 A1 | 9/2000 |
| WO | WO 00/62699 A2 | 10/2000 |
| WO | WO-0103642 A1 | 1/2001 |
| WO | WO-0232333 A1 | 4/2002 |
| WO | WO-0232334 A1 | 4/2002 |
| WO | WO 2006/058251 A2 | 6/2006 |
| WO | WO-2009082433 A2 | 7/2009 |
| WO | WO-2009137819 A1 | 11/2009 |
| WO | WO 2013/010009 A1 | 1/2013 |
| WO | WO 2013/055815 A1 | 4/2013 |
| WO | WO 2013/055826 A1 | 4/2013 |

OTHER PUBLICATIONS

An S.S., et al., "Airway Smooth Muscle Dynamics: A Common Pathway of Airway Obstruction in Asthma," European Respiratory Journal, 2007, 29 (5), 834-860.

Bel E.H., ""Hot stuff": Bronchial Thermoplasty for Asthma," American Journal of Respiratory and Critical Care Medicine, 2006, 173 (9), 941-943.

Brown R.H., et al., "Effect of Bronchial Thermoplasty on Airway Distensibility," European Respiratory Journal, 2005, 26 (2), 277-282.

(56) References Cited

OTHER PUBLICATIONS

Brown R.H., et al., "In Vivo evaluation of the Effectiveness of Bronchial Thermoplasty with Computed Tomography," Journal of Applied Physiology, 2005, 98 (5), 1603-1606.

Chhajed P.N., et al., "Will there be a Role for Bronchoscopic Radiofrequency Ablation," Journal of Bronchology, 2005, 12 (3), 184-186.

Abandoned U.S. Appl. No. 09/095,323, filed Jun. 10, 1998.

Abandoned U.S. Appl. No. 09/244,173, filed Feb. 4, 1999.

Co-pending U.S. Appl. No. 12/640,644, filed Dec. 17, 2009.

Patented U.S. Appl. No. 12/727,156, filed Mar. 18, 2010.

Patented U.S. Appl. No. 12/765,704, filed Apr. 22, 2010.

Cox G., et al., "Asthma Control during the Year after Bronchial Thermoplasty," New England journal of medicine, 2007, 356 (13), 1327-1337.

Cox G., et al., "Asthma Intervention Research (AIR) Trial Evaluating Bronchial Thermoplasty: Early Results," American Thoracic Society Annual Meeting, 2002, 1 page.

Cox G., et al., "Bronchial Thermoplasty for Asthma," American Journal of Respiratory and Critical Care Medicine, 2006, 173 (9), 965-969.

Cox G., et al., "Bronchial Thermoplasty: Long-Term Follow-Up and Patient Satisfaction," Chest, 2004, 126 (4), 822s.

Cox G., et al., "Bronchial Thermoplasty: One-Year Update, American Thoracic Society Annual Meeting," American Journal of Respiratory and Critical Care Medicine, 2004, 169, A313.

Cox G., et al., "Clinical Experience with Bronchial Thermoplasty for the Treatment of Asthma," Chest, 2003, 124, 106S.

Cox G., et al., "Development of a Novel Bronchoscopic Therapy for Asthma," Journal of Allergy and Clinical Immunology, 2003, 113 (2), S33.

Cox G., et al., "Early Clinical Experience with Bronchial Thermoplasty for the Treatment of Asthma," American Thoracic Society Annual Meeting, 2002, 1068.

Cox G., et al., "Impact of Bronchial Thermoplasty on Asthma Status: Interim Results from the AIR Trial," 2006, 1 page.

Cox G., et al., "Radiofrequency Ablation of Airway Smooth Muscle for Sustained Treatment of Asthma: Preliminary Investigations," European Respiratory Journal, 2004, 24 (4), 659-663.

Danek C.J., et al., "Bronchial Thermoplasty Reduces Canine Airway Responsiveness to Local Methacholine Challenge," American Thoracic Society Annual Meeting, 2002, 1 page.

Danek C.J., et al., "Reduction in Airway Hyperresponsiveness to Methacholine by the Application of RF Energy in Dogs," Journal of Applied Physiology, 2004, 97 (5), 1946-1953.

Dierkesmann R., "Indication and Results of Endobronchial Laser Therapy," Lung, 1990, 168, 1095-1102.

Hogg J. C., "The Pathology of Asthma," APMIS, 1997, 105 (10), 735-745.

International Search Report for Application No. PCT/US00/05412, mailed on Jun. 20, 2000, 2 pages.

International Search Report for Application No. PCT/US00/18197, mailed on Oct. 3, 2000, 1 page.

International Search Report for Application No. PCT/US00/28745, mailed on Mar. 28, 2001, 6 pages.

International Search Report for Application No. PCT/US01/32321, mailed on Jan. 18, 2002, 2 pages.

International Search Report for Application No. PCT/US98/03759, mailed on Jul. 30, 1998, 1 page.

International Search Report for Application No. PCT/US98/26227, mailed on Mar. 25, 1999, 1 page.

International Search Report for Application No. PCT/US99/00232, mailed on Mar. 4, 1999, 1 page.

International Search Report for Application No. PCT/US99/12986, mailed on Sep. 29, 1999, 1 page.

Ivanyuta O.M., et al., "Effect of Low-Power Laser Irradiation of Bronchial Mucosa on the State of Systemic and Local Immunity in Patients with Chronic Bronchitis," Problemy Tuberkuleza, 1991, 6, 26-29.

James A.L., et al., "The Mechanics of Airway Narrowing in Asthma," American Review of Respiratory Diseases, 1989, 139 (1), 242-246.

Johnson S. R., et al., "Synthetic Functions of Airway Smooth Muscle in Asthma," Trends Pharmacol. Sci., 1997, 18 (8), 288-292.

Kitamura S., "Color Atlas of Clinical Application of Fiberoptic Bronchoscopy," 1990, Year Book Medical Publishers, 2 pages.

Laviolette M., et al., "Asthma Intervention Research (Air) Trial: Early Safety Assessment of Bronchial Thermoplasty," American Journal of Respiratory and Critical Care Medicine, 2004, 169, A314.

Leff A., et al., "Bronchial Thermoplasty Alters Airway Smooth Muscle and Reduces Responsiveness in Dogs: A Possible Procedure for the Treatment of Asthma," American Thoracic Society Annual Meeting, 2002, 1 page.

Lim E.C., et al., "Botulinum Toxin: A Novel Therapeutic Option for Bronchial Asthma," Medical Hypotheses, 2006, 66 (5), 915-919.

Lombard C.M., et al., "Histologic Effects of Bronchial Thermoplasty of Canine and Human Airways," American Thoracic Society Annual Meeting, 2002, 1 page.

Macklem P. T., "Mechanical Factors Determining Maximum Bronchoconstriction," European Respiratory Journal, 1989, 6, 516s-519s.

Mayse M.L., et al., "Clinical Pearls for Bronchial Thermoplasty," Journal of Bronchology, 2007, 14 (2), 115-123.

Miller J.D., et al., "A Prospective Feasibility Study of Bronchial Thermoplasty in the Human Airway," Chest, 2005, 127 (6), 1999-2006.

Miller J.D., et al., "Bronchial Thermoplasty is Well Tolerated by Non-Asthmatic Patients Requiring Lobectomy," American Thoracic Society Annual Meeting, 2002, 1 page.

Mitzner W., "Airway Smooth Muscle the Appendix of the Lung," American Journal of Respiratory and Critical Care Medicine, 2004, 169 (7), 787-790.

Netter F.H., "Respiratory System: A Compilation of Paintings Depicting Anatomy and Embryology, Physiology, Pathology, Pathophysiology, and Clinical Features and Treatment of Diseases,in the CIBA Collection of Medical Illustrations M.B. Divertie, ed., Summit: New Jerse," 1979, 7, 119-135.

Notice of final Rejection, Japanese Patent Application No. 2000-553172, dated Sep. 2, 2008, 5 pages.

Provotorov V.M., et al., "The Clinical Efficacy of Treating Patients with Nonspecific Lung Diseases Using Low-energy Laser Irradiation and Intrapulmonary Drug Administration," Terapevticheskii Arkhiv, 1991, 62 (12), 18-23.

Rubin A., et al., "Bronchial Thermoplasty Improves Asthma Status of Moderate to Severe Perisstent Asthmatics Over and Above Current Standard-of-Care," American College of Chest Physicians, 2006, 2 pages.

Shesterina M.V., et al., "Effect of Laser Therapy on Immunity in Patients with Bronchial Asthma and Pulmonary Tuberculosis," Problemy Tuberkuleza, 1994, 5, 23-26.

Solway J., et al., "Airway Smooth Muscle as a Target for Asthma Therapy," New England Journal of medicine, 2007, 356 (13), 1367-1369.

Sterk P.J., et al., "Heterogeneity of Airway Hyperresponsiveness: Time for Unconventional, But Traditional, Studies," Journal of Applied Physiology, 2004, 96 (6), 2017-2018.

Toma T.P., et al., "Brave New World for Interventional Bronchoscopy," Thorax, 2005, 60 (3), 180-181.

Trow T.K., "Clinical Year in Review I: Diagnostic Imaging, Asthma, Lung Transplantation, and Interventional Pulmonology," Proceedings of the American Thoracic Society, 2006, 3 (7), 553-556.

Vasilotta P.L., et al., "I-R Laser: A New Therapy in Rhino-Sino-Nasal Bronchial Syndrome with Asthmatic Component," American Society for Laser Medicine and Surgery Abstracts, 74. 1993.

(56) References Cited

OTHER PUBLICATIONS

Vorotnev A.I., et al., "The Treatment of Patients with Chronic Obstructive Bronchitis by Using a Low-power Laser at a General Rehabilitation Center," Terapevticheskii Arkhiv, 1997, 69 (3), 17-19.

Wiggs B.R., et al., "On the Mechanism of Mucosal Folding in Normal and Asthmatic Airways," Journal of Applied Physiology, 1997, 83 (6), 1814-1821.

Wilson S.R., et al., "Global Assessment after Bronchial Thermoplasty: The Patients Perspective," Journal of Outcomes Research, 2006, 10, 37-46.

Wizeman W., et al., "A Computer Model of Thermal Treatment of Airways by Radiofrequency (RF) Energy Delivery," American Thoracic Society Annual Meeting, 2007, 1 page.

* cited by examiner

DEVICES AND METHODS FOR DELIVERING ENERGY TO BODY LUMENS

CROSS-REFERENCE TO RELATED APPLICATIONS

This application claims the benefit of priority from U.S. Provisional Application No. 61/722,499, filed on Nov. 5, 2012, the entirety of which is incorporated by reference herein.

TECHNICAL FIELD

Various embodiments of the present disclosure relate generally to medical devices and related methods. More specifically, particular embodiments of the present disclosure relate to devices and methods for delivering energy to a body lumen.

BACKGROUND

Asthma is a disease in which (i) bronchoconstriction, (ii) excessive mucus production, and/or (iii) inflammation and swelling of airways can occur, potentially causing widespread but variable airflow obstruction, thereby making it difficult for the asthma sufferer to breathe. Asthma is a chronic disorder, primarily characterized by persistent airway inflammation. However, asthma is further characterized by acute episodes of additional airway narrowing via contraction of hyper-responsive airway smooth muscle.

Asthma may be managed pharmacologically by, among other things: (1) long-term control through use of anti-inflammatories and long-acting bronchodilators, and (2) short-term management of acute exacerbations through use of short-acting bronchodilators. Both of these approaches can require repeated and regular use of the prescribed drugs. High doses of corticosteroid anti-inflammatory drugs can have serious side effects that require careful management. In addition, some patients are resistant to steroid treatment. The difficulty involved in patient compliance with pharmacologic management and the difficulty of avoiding stimulus that triggers asthma are common barriers to successful asthma management.

Current management techniques are neither completely successful nor free from side effects. Presently, a new treatment for asthma is showing promise. This treatment comprises the application of energy to the airway smooth muscle tissue. Additional information about this treatment may be found in commonly assigned patents and applications, including U.S. Pat. Nos. 6,411,852 and 6,634,363, and U.S. Published Application Nos. US-2005-0010270-A1 and US-2002-0091379-A1, the entirety of each of which is incorporated herein by reference.

The application of energy to airway smooth muscle tissue, when performed via insertion of a treatment device into the bronchial passageways, requires, among other things, navigation through tortuous anatomy (e.g., curved lung passages) as well as the ability to treat a variety of sizes of bronchial passageways. As discussed in the above referenced patents and applications, use of an RF energy delivery device is one means of treating smooth muscle tissue within the bronchial passageways.

FIG. 1 illustrates an exemplary bronchial tree 90. As noted herein, devices treating areas of the lungs must have a construction that enables navigation through the tortuous airway passages. As shown, the various bronchioles 92 extend from right and left bronchi 94, and decrease in size and have many branches 96. Accordingly, an efficient treatment requires devices that are able to treat airways of varying sizes as well as function properly when repeatedly deployed after navigating through the tortuous anatomy.

Tortuous anatomy also poses challenges when the treatment device requires mechanical actuation of the treatment portion (e.g., expansion of a treatment element at a remote site). In particular, attempting to actuate a member may be difficult in view of the fact that the force applied at the operator's hand-piece must translate to the distal end of the device. The strain on the operator is further intensified given that the operator must actuate the distal end of the device many times to treat various portions of the anatomy. When a typical device is contorted after being advanced to a remote site in the lungs, the resistance within the device may be amplified given that internal components are forced together.

In addition to basic considerations of navigation and site access, there exists the matter of device orientation and tissue contact at the treatment site. Many treatment devices make contact or are placed in close proximity to the target tissue. Yet, variances in the construction of the treatment device may hinder proper alignment or orientation of the device. For example, in the case of a device having an expandable basket-type energy delivery element that is deployed intralumenally, the treatment area may benefit from uniform contact of basket elements around the perimeter of the lumen. However, in this case, design or manufacturing variances may tend to produce a device where the angle between basket elements may not be uniform. This problem tends to be exacerbated after repeated actuation of the device and/or navigating the device through tortuous anatomy when the imperfections of the device become worsened through plastic deformation of the individual components.

For many treatment devices, the distortion of the energy delivery elements might cause variability in the treatment effect. For example, many RF devices heat tissue based on the tissue's resistive properties. Increasing or decreasing the surface contact between the electrode and tissue often increases or decreases the amount of current flowing through the tissue at the point of contact. This directly affects the extent to which the tissue is heated. Similar concerns may also arise with resistive heating elements, devices used to cool the airway wall by removing heat, or any energy delivery device. In any number of cases, variability of the energy delivery/tissue interface may cause variability in treatment results. The consequential risks range from an ineffective treatment to the possibility of patient injury.

Furthermore, most medical practitioners recognize the importance of establishing acceptable contact between the energy delivery element and tissue. Therefore, distortion of the energy delivery element or elements increases the procedure time when the practitioner spends an inordinate amount of time adjusting a device to compensate for or avoid such distortion. Such action becomes increasingly problematic in those cases where proper patient management limits the time available for the procedure.

For example, if a patient requires an increasing amount of medication (e.g., sedatives or anesthesia) to remain under continued control for performance of the procedure, then a medical practitioner may limit the procedure time rather than risk overmedicating the patient. As a result, rather than treating the patient continuously to complete the procedure, the practitioner may plan to break the procedure in two or more sessions. Subsequently, increasing the number of sessions poses additional consequences on the part of the patient in cost, the residual effects of any medication, adverse effects of the non-therapeutic portion of the procedure, etc.

In view of the above, the present methods and devices described herein provide an improved means for treating tortuous anatomy such as the bronchial passages. It is noted that the improvements of the present device may be beneficial for use in other parts of the anatomy as well as the lungs.

SUMMARY

In accordance with certain embodiments of the present disclosure, a medical device is disclosed for delivering energy to a body lumen. The device includes an elongate member including a proximal portion and a distal portion adapted for insertion into a body lumen; and an energy delivery device disposed adjacent the distal portion of the elongate member, the energy delivery device including at least one elongate electrode arm, wherein the elongate electrode arm is configured to transition between a first configuration and a second configuration different than the first configuration. The at least one elongate electrode arm includes an active region configured to contact and deliver energy to the body lumen, wherein the active region is disposed between a proximal end region and a distal end region of the elongate electrode arm. When the elongate electrode arm is in the first configuration, at least a portion of the active region of the elongate electrode arm extends radially inward toward a longitudinal axis of the energy delivery device.

In accordance with certain embodiments of the present disclosure, a medical device is disclosed for delivering energy to a passageway of a patient's lung. The device includes an elongate member having a proximal end, a distal end, and a lumen extending therebetween; and a basket assembly adjacent the distal end and configured to transition between a collapsed state and an expanded state, wherein the basket assembly includes a plurality of expandable legs, wherein at least one of the expandable legs includes an active region configured to contact and deliver energy to a wall of the passageway when the basket assembly is in the expanded state. When the basket assembly is in the collapsed state, at least a portion of the active region of the at least one of the expandable legs includes an inwardly concave configuration.

In accordance with certain embodiments of the present disclosure, a medical device is disclosed for delivering energy to a body lumen. The device includes a flexible elongate member comprising a proximal portion and a distal portion adapted for insertion into a body lumen; and an energy delivery device disposed adjacent the distal portion of the elongate member, the energy delivery device comprising at least one elongate electrode and being configured to move between an expanded state and a collapsed state. The at least one elongate electrode comprises an active region configured to contact and deliver energy to the body lumen when the energy delivery device is in the expanded state. When the energy delivery device is in the collapsed state, at least a portion of the active region of the elongate electrode bows radially inward toward a longitudinal axis of the energy delivery device, such that at least a portion of the active region is closer to the longitudinal axis than at least a portion of the proximal adjoining region and at least a portion of the distal adjoining region. Upon the application of axial compressive forces to the elongate electrode, the elongate electrode is configured to bow outward away from the longitudinal axis of the energy delivery device.

The disclosed embodiments may include one or more of the following features: the at least one elongate electrode arm may include a plurality of elongate electrode arms; the plurality of elongate electrode arms may be secured together to form a basket assembly; the basket assembly may be self-expandable; the elongate electrode arm may be configured to transition from the first configuration to the second configuration when an axially compressive force is applied to the elongate electrode arm; when the elongate electrode arm is in the first configuration, the elongate electrode arm may include a substantially concave configuration; when the elongate electrode arm is in the second configuration, the active region of the elongate electrode arm may include a substantially planar configuration; a member configured to apply an axially compressive force to the at least one elongate electrode; the at least one elongate electrode arm may be formed of a shape memory material; the proximal end region and the distal end region of the elongate electrode arm may include an insulating coating; the active region may include an electrode secured to the elongate electrode arm; the active region may include an electrode secured to the at least one expandable leg; when the basket assembly is in the expanded configuration, the active region of the at least one of the expandable legs may include a substantially planar configuration; the active region of the at least one of the expandable legs may be disposed between a proximal leg portion and a distal leg portion; the proximal and distal leg portions may include an insulating coating; the proximal adjoining region and the distal adjoining region are either substantially flat or bow radially inward toward the longitudinal axis of the energy delivery device; when the energy delivery device is in the expanded state, the active area becomes substantially planar, and at least a portion of the active region becomes positioned farther from the longitudinal axis than at least the portion of the proximal adjoining region and at least the portion of the distal adjoining region; the at least one elongate electrode comprises a plurality of elongate electrodes that form an expandable basket assembly.

The present disclosure describes devices configured to treat the airways or other anatomical structures, and may be especially useful in tortuous anatomy. The devices described herein are configured to treat with uniform or predictable contact (or near contact) between an active element and tissue. Typically, the disclosed devices allow this result with little or no effort by a physician. Accordingly, aspects of the disclosed embodiments offer increased effectiveness and efficiency in carrying out a medical procedure. The increases in effectiveness and efficiency may be especially apparent in using devices having relatively longer active end members.

In view of the above, a variation of the disclosed device includes a catheter for use with a power supply, the catheter comprising a flexible elongate shaft coupled to at least one energy delivery element that is adapted to apply energy to the body lumen. The shaft will have a flexibility to accommodate navigation through tortuous anatomy. The energy delivery elements are described below and include basket type design, or other expandable designs that permit reduction in size or profile to aid in advancing the device to a particular treatment site and then may be expanded to properly treat the target site. The basket type designs may be combined with expandable balloon or other similar structures.

Variations of the device can include an elongate sheath having a near end, a far end adapted for insertion into the body, and having a flexibility to accommodate navigation through tortuous anatomy, the sheath having a passageway extending therethrough, the passageway having a lubricious layer extending from at least a portion of the near end to the far end of the sheath, where the shaft is slid ably located within the passageway of the sheath.

Variations of devices described herein can include a connector for coupling the energy delivery element to the power supply. The connector may be any type of connector commonly used in such applications. Furthermore, the connector may include a cable that is hard-wired to the catheter and connects to a remote power supply. Alternatively, the connector may be an interface that connects to a cable from the power supply.

Variations of the device allow for reduced friction between the shaft and sheath to allow relatively low force advancement of a distal end of the shaft out of the far end of the sheath for advancement the energy delivery element. Additional variations of the disclosed embodiments include devices allowing for repeatable deployment of the expandable energy delivery element while maintaining the orientation and/or profile of the components of the energy delivery element. One such example includes an energy delivery basket comprising a plurality of arms, each arm having a distal end and a proximal end, each arm having a flexure length that is less than a full length of the arm.

An additional variation of the device includes a catheter for use in tortuous anatomy to deliver energy from a power supply to a body passageway. Such a catheter includes an expandable energy delivery element having a reduced profile for advancement and an expanded profile to contact a surface of the body passageway and an elongate shaft having a near end, a far end adapted for insertion into the body, the expandable energy delivery element coupled to the far end of the shaft, the shaft having a length sufficient to access remote areas in the anatomy. The design of this shaft includes column strength sufficient to advance the expandable energy delivery element within the anatomy, and a flexibility that permits self-centering of the energy delivery element when expanded to contact the surface of the body passageway.

Additional objects and advantages of the disclosed embodiments will be set forth in part in the description that follows, and in part will be apparent from the description, or may be learned by practice of the disclosed embodiments. The objects and advantages of the disclosed embodiments will be realized and attained by means of the elements and combinations particularly pointed out in the appended claims.

It is to be understood that both the foregoing general description and the following detailed description are exemplary and explanatory only and are not restrictive of the disclosed embodiments, as claimed.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

DETAILED DESCRIPTION

Reference will now be made in detail to the exemplary embodiments of the disclosure, examples of which are illustrated in the accompanying drawings. Wherever possible, the same reference numbers will be used throughout the drawings to refer to the same or like parts.

It is understood that the examples below discuss uses in the airways of the lungs. However, unless specifically noted, the disclosed embodiments are not limited to use in the lung. Instead, the disclosed embodiments may have applicability in various parts of the body, including, but not limited to, urological, biliary, and gastrointestinal applications. Moreover, the disclosed embodiments may be used in various procedures where the benefits of the device are desired.

Figure 1:
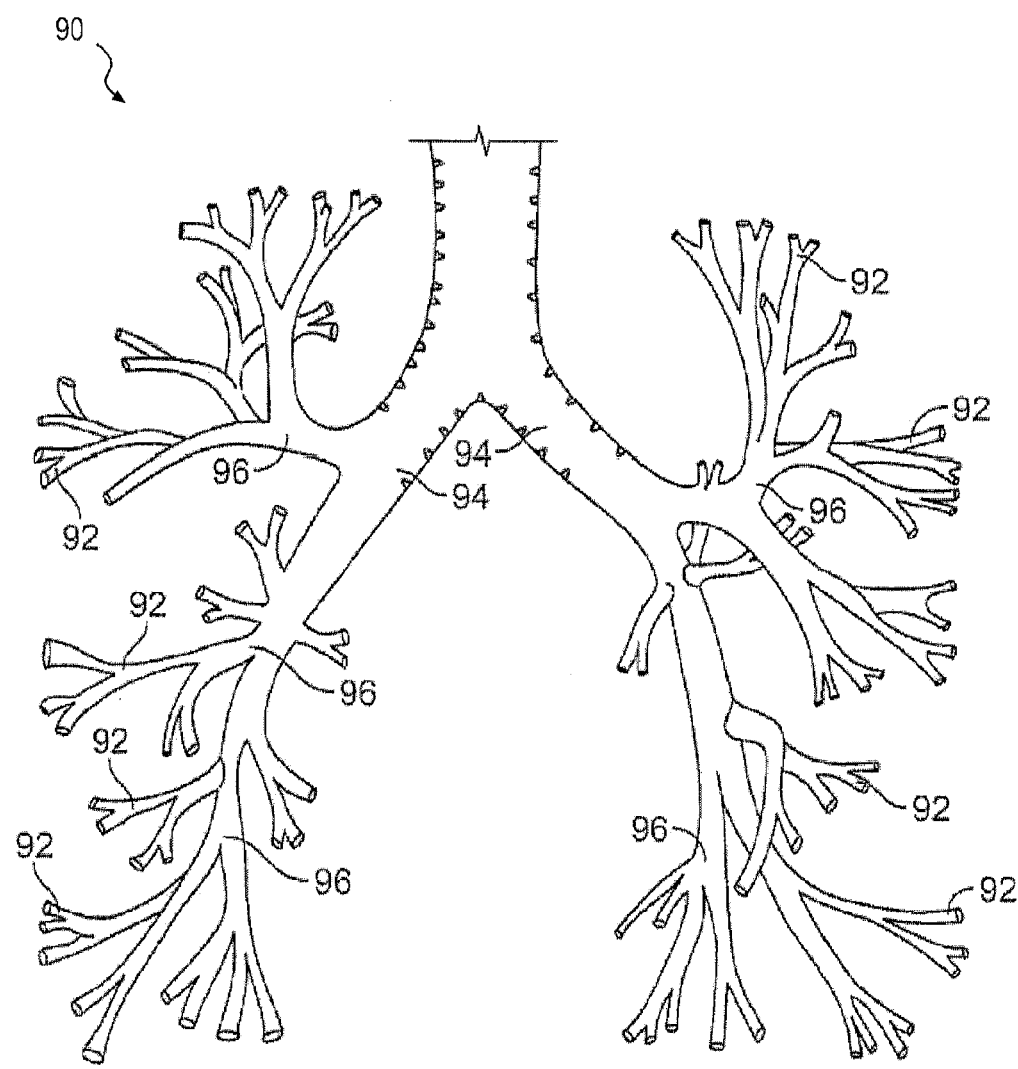
FIG. 1 is an illustration of a person's bronchial passageways.
Figure 2:
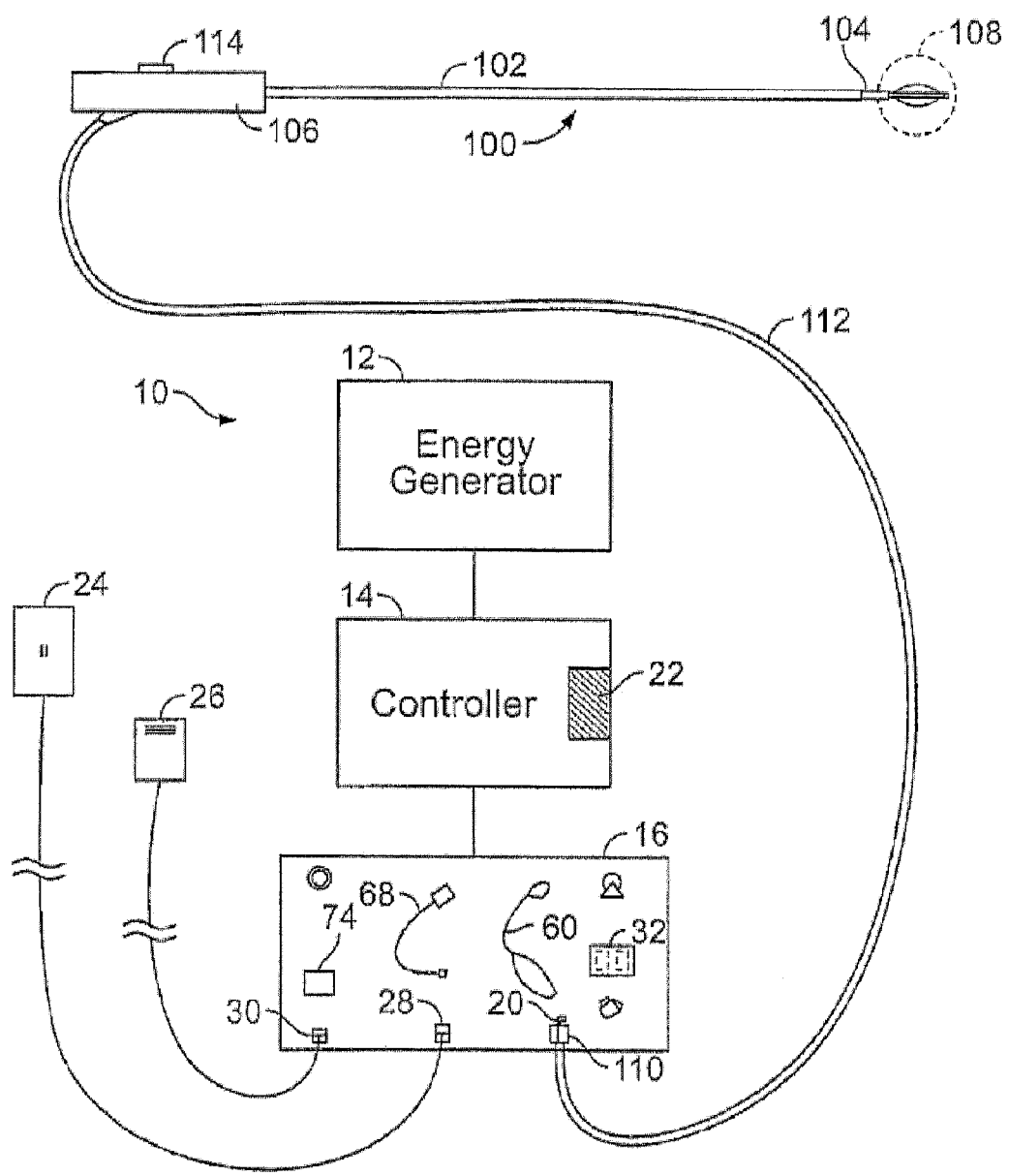
FIG. 2 is a diagram of an exemplary energy delivery system consistent with embodiments of the present disclosure.

FIG. 2 shows a schematic diagram of one example of a system 10 for delivering therapeutic energy to tissue of a patient for use with the device described herein. The illustrated variation shows the system 10 having a power supply (e.g., consisting of an energy generator 12), a controller 14 coupled to the energy generator, and a user interface surface 16 in communication with the controller 14. It is noted that the device may be used with a variety of systems (having the same or different components). For example, although variations of the device shall be described as RF energy delivery devices, some embodiments of the device may include resistive heating systems, infrared heating elements, microwave energy systems, focused ultrasound, cryo-ablation, or any other energy system. It is noted that the devices described should have sufficient length to access the tissue targeted for treatment. For example, it is presently believed necessary to treat airways as small as 3 mm in diameter to treat enough airways for the patient to benefit from the described treatment (however, it is noted that the disclosed embodiments are not limited to any particular size of airways and airways smaller or larger than 3 mm may be treated with the embodiments disclosed herein). Accordingly, devices for treating the lungs must be sufficiently long to reach deep enough into the lungs to treat these airways. Accordingly, the length of the sheath/shaft of the device that is designed for use in the lungs may be between 1.5-3 ft. long in order to reach the targeted airways.

The particular system 10 depicted in FIG. 2 is one having a user interface as well as safety algorithms that are useful for the asthma treatment discussed above. Additional information on such a system may be found in U.S. Provisional application No. 60/674,106, filed Apr. 21, 2005, entitled CONTROL METHODS AND DEVICES FOR ENERGY DELIVERY, the entirety of which is incorporated by reference herein.

Referring again to FIG. 2, a variation of a device 100 described herein includes a flexible sheath 102, an elongate shaft 104 (in this example, the shaft extends out from the distal end of the sheath 102), and a handle or other operator interface 106 (optional) secured to a proximal end of the sheath 102. The distal portion of the device 100 includes an energy delivery element 108 (e.g., an electrode, a basket electrode, a resistive heating element, cyroprobe, etc.). Additionally, the device 100 includes a connector 110 common to such energy delivery devices. The connector 110 may be integral to the end of a cable 112 as shown, or the connector 110 may be fitted to receive a separate cable 112. In any case, the device may be configured for attachment to the power supply via some type connector 110. The elongate portions 102, 104 of the device 100 may also be configured and sized to permit passage through the working lumen of a commercially available bronchoscope or endoscope. As discussed herein, the device 100 is often used within an endoscope, bronchoscope, or similar device. However, the device 100 may also be advanced into the body with or without a steerable catheter, in a minimally invasive procedure or in an open surgical procedure, and with or without the guidance of various vision or imaging systems.

FIG. 2 also illustrates additional components used in variations of the system 10. Although the depicted systems are shown as RF-type energy delivery systems, it is noted that the disclosed embodiments are not limited as such. Other energy delivery configurations contemplated may include or not require some of the elements described below. The power supply (usually the user interface portion 16) shall have connections 20, 28, 30 for the device 100, return electrode 24 (if the system 10 employs a monopolar RF configuration), and actuation pedal(s) 26 (optional). The power supply and controller may also be configured to deliver RF energy to an energy delivery element configured for bipolar RF energy delivery. The user interface 16 may also include visual prompts 32, 60, 68, 74 for user feedback regarding setup or operation of the system. The user interface 16 may also employ graphical representations of components of the system, audio tone generators, as well as other features to assist the user with system use.

In many variations of the system, the controller 14 may include a processor 22 that is generally configured to accept information from the system and system components, and process the information according to various algorithms to produce control signals for controlling the energy generator 12. The processor 22 may also accept information from the system 10 and system components, process the information according to various algorithms and produce information signals that may be directed to the visual indicators, digital display or audio tone generator of the user interface in order to inform the user of the system status, component status, procedure status or any other useful information that is being monitored by the system. The processor 22 of the controller 14 may be a digital IC processor, analog processor, or any other suitable logic or control system that carries out the control algorithms, such as those described in U.S. Provisional application No. 60/674,106, filed Apr. 21, 2005, entitled CONTROL METHODS AND DEVICES FOR ENERGY DELIVERY, the entirety of which is incorporated by reference herein.

FIG. 2 illustrates one example of an energy delivery element 108. In this example, the energy delivery element 108 includes a "basket"-like configuration that implements actuation for expansion of the basket in diameter via a slide mechanism 114 on the handle 106. For example, an operator may manipulate slide mechanism 114, which, through some type of linkage, causes electrode wires of energy delivery element 108 to expand radially outward or otherwise mechanically deploy. Alternatively, the basket may be configured to expand as soon as it is exposed by a sheath, due to its own resilient forces (i.e., making it "self-expandable"). Such features may be useful when the device is operated intraluminally or in anatomy such as the lungs due to the varying size of the bronchial passageways that may require treatment.

Figure 3:
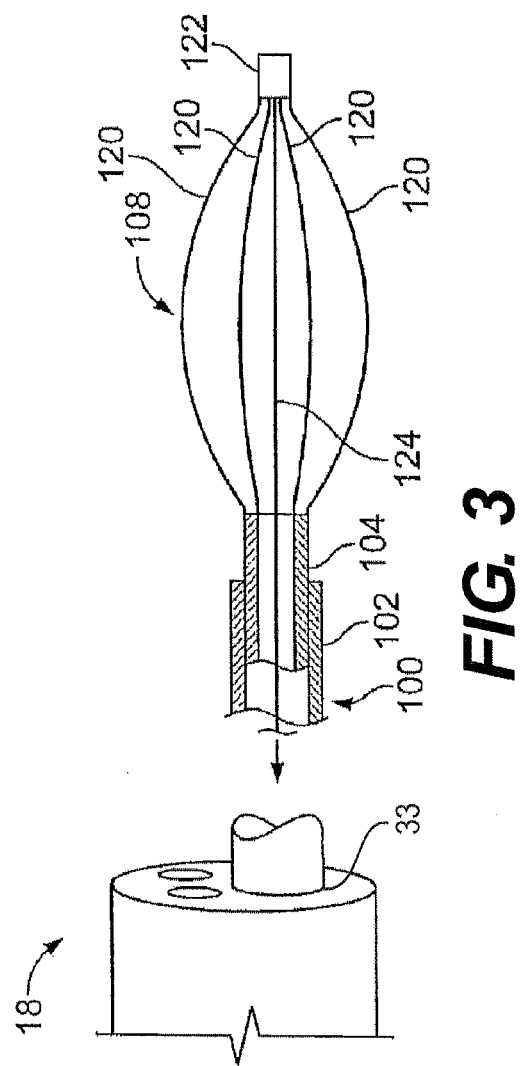
FIG. 3 is a diagram of an exemplary energy delivery device consistent with embodiments of the present disclosure.

FIG. 3 illustrates an embodiment in which device 100 may be advanced through a working channel 33 of a bronchoscope 18. While a bronchoscope 18 may assist in the procedure, the device 100 may be used through direct insertion or other insertion means as well. In addition, FIG. 3 illustrates an embodiment of energy delivery element 108 in a basket configuration and including a number of arms 120 that carry electrodes (not shown). In this embodiment, the arms 120 are attached to the elongated shaft 104 at a proximal end while the distal end of the arms 120 are affixed to a distal tip 122. In one embodiment, the arms 120 may be "tipless", whereby the arms 120 do not terminate in distal tip 120 but instead "double back" on themselves, forming one or more loops within distal tip 122. To actuate the energy delivery element 108, a wire or tether 124 may be affixed to the distal tip 122 to enable compression of the arms 120 between the distal tip 122 and elongate shaft 104. When the energy delivery element 108 is actuated, i.e., expanded, the arms 120 may bow outward, away from a longitudinal axis of the energy delivery element 108.

Figure 4:
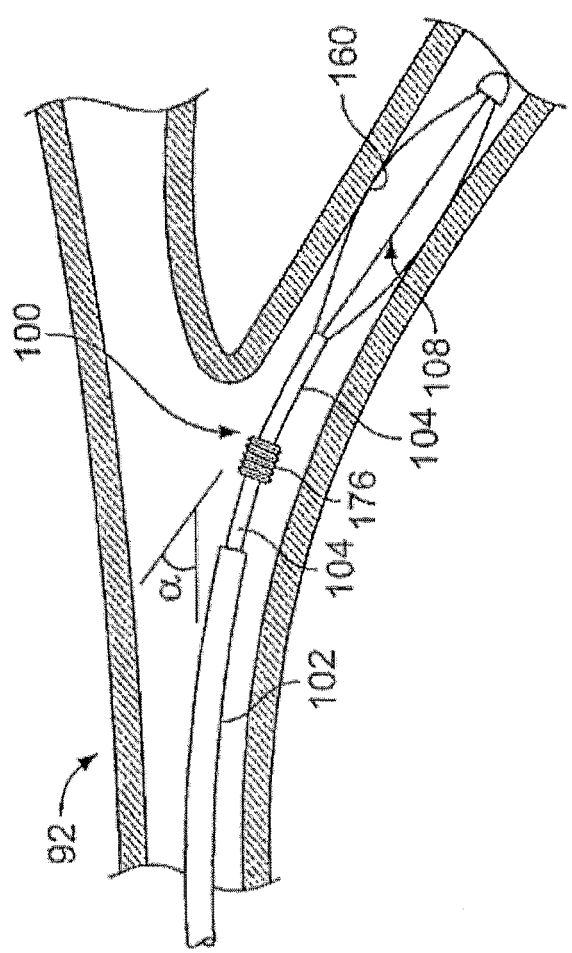
FIG. 4 is a diagram of an exemplary energy delivery device disposed in a person's bronchial passageway.

FIG. 4 depicts an example of device 100, including energy delivery element 108, being advanced thorough a body lumen 92, e.g., a bronchial passageway. In one embodiment, as shown in FIG. 4, device 100 may also incorporate a junction 176 that adjusts for misalignment between the branching airways or other body passages, thereby allowing alignment of the device to closely match the alignment of the airway. It is noted that the present feature also benefits those cases in which the pathway and target site are offset as opposed to having an angular difference. The junction 176 helps to eliminate the need for alignment of the axis of the active element 108 with the remainder of the device in order to provide substantially even tissue contact. The junction may be a joint, a flexure, or equivalent means. FIG. 4 illustrates an example of where the access passageway and passageway to be treated are misaligned by an angle alpha ($\alpha$). Yet, the energy delivery element 108 of the treatment device 100 remains substantially aligned with the target area.

Figure 5:
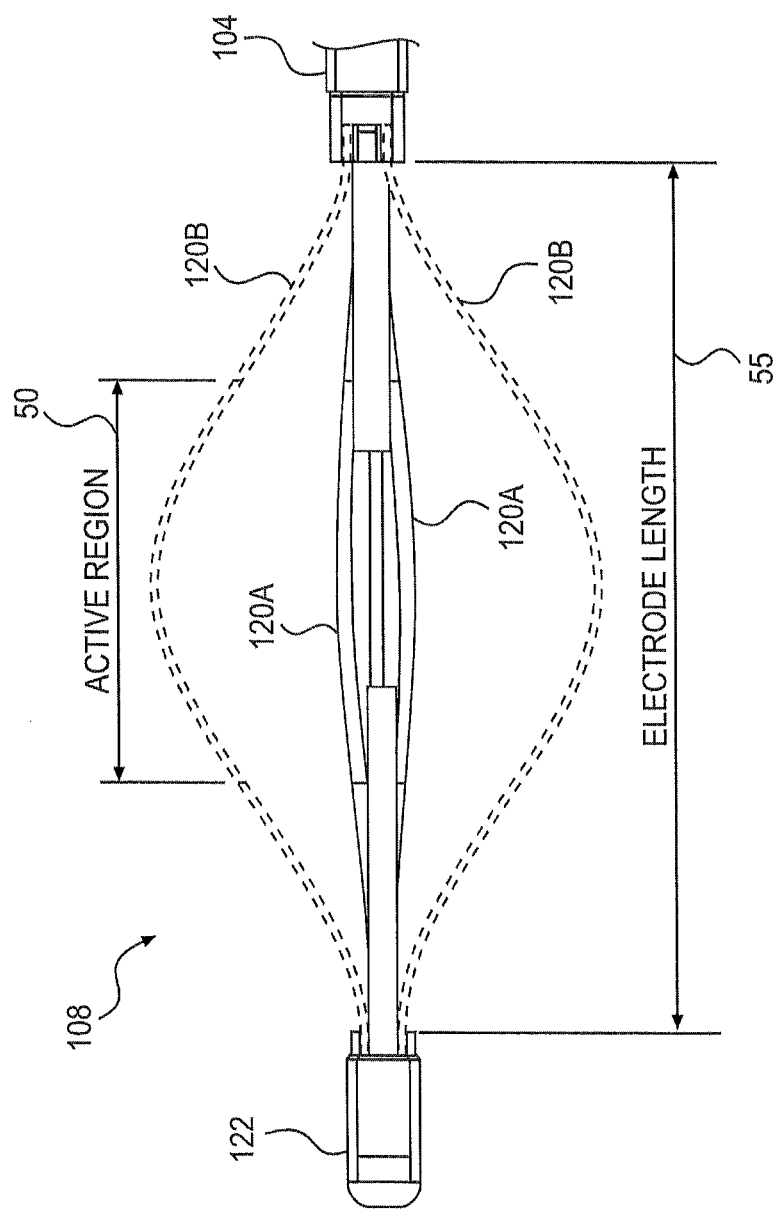
FIG. 5 is a cross-sectional diagram of an exemplary energy delivery device.

FIG. 5 depicts an embodiment of energy delivery element 108 in a collapsed configuration (electrode arms 120A) and expanded configuration (electrode arms 120B). Specifically, the electrode arms of energy delivery element 108 may be originally shaped like electrode arms 120A, as shown in FIG. 5, when energy delivery element 108 is in a collapsed configuration. The electrode arms may be deformed to the shape of electrode arms 120B.

FIG. 5 depicts an embodiment of energy delivery element 108 including a representation of an active region 50. Active region 50 of electrode arms 120A/120B may be a conductive region of electrode arms 120A/120B. For example, the electrodes may be generally metallic or otherwise conductive, and have an insulator disposed around the electrodes in all areas other than the active region 50. Alternatively, electrode arms 120A/120B may have a special metallic coating or other conductive material applied to electrode arms 120A/120B around the active region 50. As discussed above, the active region 50 may be configured to contact and apply energy to the tissue of a body lumen. In the energy delivery element 108 of FIG. 5, the initial shape of collapsed electrode arms 120A, and therefore the resulting shape of expanded electrode arms 120B, may cause only a subset of active region 50 to contact and apply energy to the body lumen tissue. In other words, the "contact area" may be generally shorter than desired, and/or less of the active region 50 than desired.

Electrode arms 120A/B of the energy delivery element 108 may have various cross-sectional shapes. For example, the shapes may be round, rounded or polygonal in cross section. Additionally, each electrode arm may change cross section along its axis, providing for, for example, electrodes that are smaller or larger in cross section than the distal and proximal portions of each electrode arm. This would provide a variety of energy delivery characteristics and bending profiles, allowing the design to be improved such that longer or wider electrode configurations can be employed. For example, if the cross-sectional thickness of the active portion of the electrode arm is greater than the cross-sectional thickness of the distal and proximal (i.e., inactive) portions of the electrode arm, the electrode arm would be predisposed to bow outward in the distal and proximal sections, while remaining flatter in the active area of the electrode arm, potentially providing improved tissue contact.

One objective of the present disclosure involves increasing the amount of active region 50 that contacts a body lumen, e.g., to promote more uniform contact between the energy delivery elements 108 and a treated body lumen. Another objective of the present disclosure involves increasing the ratio of the contact area to the active region 50; and/or a ratio of the contact area to the electrode length 55. Traditionally, the active region 50 may be substantially curved along its entire length, causing only around 5 mm of the active region 50 to constitute "contact area" with the body lumen. For example, traditional energy delivery elements 108 may form a shape that is naturally formed by a straight wire that is compressed or otherwise urged to bow outwardly near its midpoint. Accordingly, in one exemplary embodiment, electrode arms 120 of energy delivery element 108 may be pre-bent or pre-shaped before being expanded into a basket configuration.

Referring now to FIGS. 6A-8B, the electrode arms of energy delivery element 108 may be pre-shaped as already described herein. In particular, the electrode arms 120 may be pre-shaped to control the direction in which the arms deflect upon basket deployment 108 to prevent electrode inversion, provide controlled buckling of the basket electrode 108, and improve tissue contact.

Figure 6A:
FIGS. 6A-6B depict exemplary pre-shaped energy delivery electrode wires.

FIG. 6A illustrates a pre-bent electrode arm 600, which is pre-bent according to existing techniques. For example, the electrodes may be constructed of a suitable current conducting metal or alloys such as, for example, copper, steel, and platinum. The electrodes may also be constructed of a shape memory alloy which is capable of assuming a predetermined, i.e., programmed, shape upon reaching a predetermined, i.e., activation, temperature. Such metals are known in the art as described, for example, in U.S. Pat. Nos. 4,621,882 and 4,772,112, which are incorporated herein. For the presently disclosed embodiments, the shape memory metal used may have the characteristic of assuming a deflection away (i.e., expands) from a device longitudinal axis when activated, i.e., heated in excess of the normal body temperature and preferably between 60° C. and 95° C. One suitable shape memory alloy is available as NITINOL from Raychem Corp., Menlo Park, Calif.

Figure 6B:

As shown in FIG. 6B, when axial compressive loads are applied to the electrode 600 during deployment, the pre-shaped arm is predisposed to buckle or deflect in a predictable, desired outwards direction into electrode arm 600', to make contact with the airway wall. Hence, the pre-shaped arm 600 provides for preferential buckling in the outward direction, thereby forming expanded electrode arm 600', which is of use in tortuous airways where orthogonal or side loads commonly cause arm inversions. At all points along its length, the pre-shaped arm 600 is either straight or bows outward from a longitudinal axis of an energy delivery element. However, as described above, the configuration of FIG. 6A-6B may result in a tissue contact area of expanded electrode arm 600' that is shorter and less uniform than desired, and/or a smaller proportion of active area 50 than desired.

Figure 7A:
FIGS. 7A-7B depict exemplary pre-shaped energy delivery electrode wires consistent with embodiments of the present disclosure.
Figure 7B:
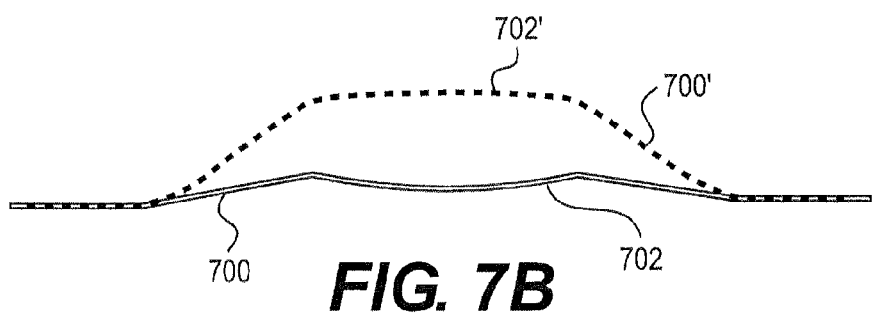

Accordingly, several alternative pre-shaped electrode arms are disclosed, which may be employed to induce more desirable bowing or buckling upon the application of axial compression, so that an entire active area may make contact with a patient's tissue. FIG. 7A depicts an embodiment of a pre-shaped electrode arm 700 having an active area 702 that bows inward toward a longitudinal axis of the energy delivery device, when in a collapsed configuration. In other words, the active area 702 is pre-shaped to be convex from a perspective of the longitudinal axis of the energy delivery device, and concave from a perspective away from the energy delivery device. As a result of the concavity, or inward bowing, of active area 702, axial compressive forces on electrode arm 700 cause electrode arm 700 to deform to the shape depicted as electrode arm 700' of FIG. 7B. Specifically, as depicted in FIG. 7B, axial compressive forces on electrode arm 700 cause the electrode arm 700, including concave active area 702, to form an expanded electrode arm 700' having a desirable active area 702'. Concave active area 702 may flatten to form a substantially flat active area 702' by virtue of torque transferred from end portions of electrode arm 700 to the concave active area 702, upon the application of axial forces (e.g., from wire or tether 124 applying tension, as described above).

By comparison between FIGS. 6B and 7B, it can be seen that expanded electrode arm 700' may form a longer and more uniform contact area as compared to the contact area of expanded electrode arm 600'. In addition, expanded electrode arm 700' may form a flatter active area 700' than the active area of expanded electrode arm 600', thereby also causing longer, and more uniform contact area. In one embodiment, the contact area of expanded electrode arm 700' may be approximately 5-15 mm in length. Because of the pre-formed concavity in electrode arm 700, the shape of active area 702' on expanded electrode arm 700', and resulting lengthened contact area, may promote more uniform contact between the device active area 702' and the tissue targeted for energy delivery. For example, the shape of expanded electrode arm 700' may provide desirable and consistent tissue contact over a substantial entirety of active area 702'.

Figure 8A:
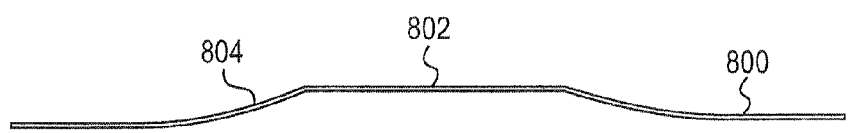
FIGS. 8A-8B depict exemplary pre-shaped energy delivery electrode wires consistent with embodiments of the present disclosure.
Figure 8B:
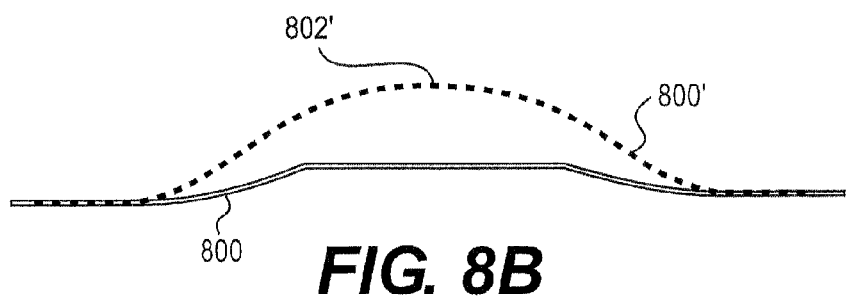

FIG. 8A depicts an electrode arm 800 having a flat active area 802 and concave adjoining portions 804. As a result of the concavity, or inward bowing, of adjoining portions 804, axial compressive forces on electrode arm 800 may cause electrode arm 800 to deform to the shape depicted as electrode arm 800', as shown in FIG. 8B. Specifically, as depicted in FIG. 8B, axial compressive forces on electrode arm 800 causes the electrode arm 800; including concave adjoining portions 804, to form an expanded electrode arm 800' having an active area 802'. Concave adjoining portions 804 may expand to form longer active area 802' by virtue of torque transferred from end portions of electrode arm 800 to active area 802 and adjoining portions 804, upon the application of axial forces (e.g., from wire or tether 124 applying compression, as described above).

By comparison between FIGS. 6B and 8B, it can be seen that expanded electrode arm 800' may form a longer and more uniform contact area as compared to the contact area of expanded electrode arm 600'. In addition, expanded electrode arm 800' may form a flatter active area 800' than the active area of expanded electrode arm 600', thereby also causing longer, and more uniform contact area. In one embodiment, the contact area of expanded electrode arm 800' may be approximately 5-15 mm in length. Because of the pre-formed concavity in adjoining portions of electrode arm 800, the shape of active area 802' on expanded electrode arm 800', and resulting lengthened contact area, may promote more uniform contact between the device active area 802' and the tissue targeted for energy delivery. For example, the shape of expanded electrode arm 800' may provide desirable and consistent tissue contact over a substantial entirety of active area 802'.

Figure 9:
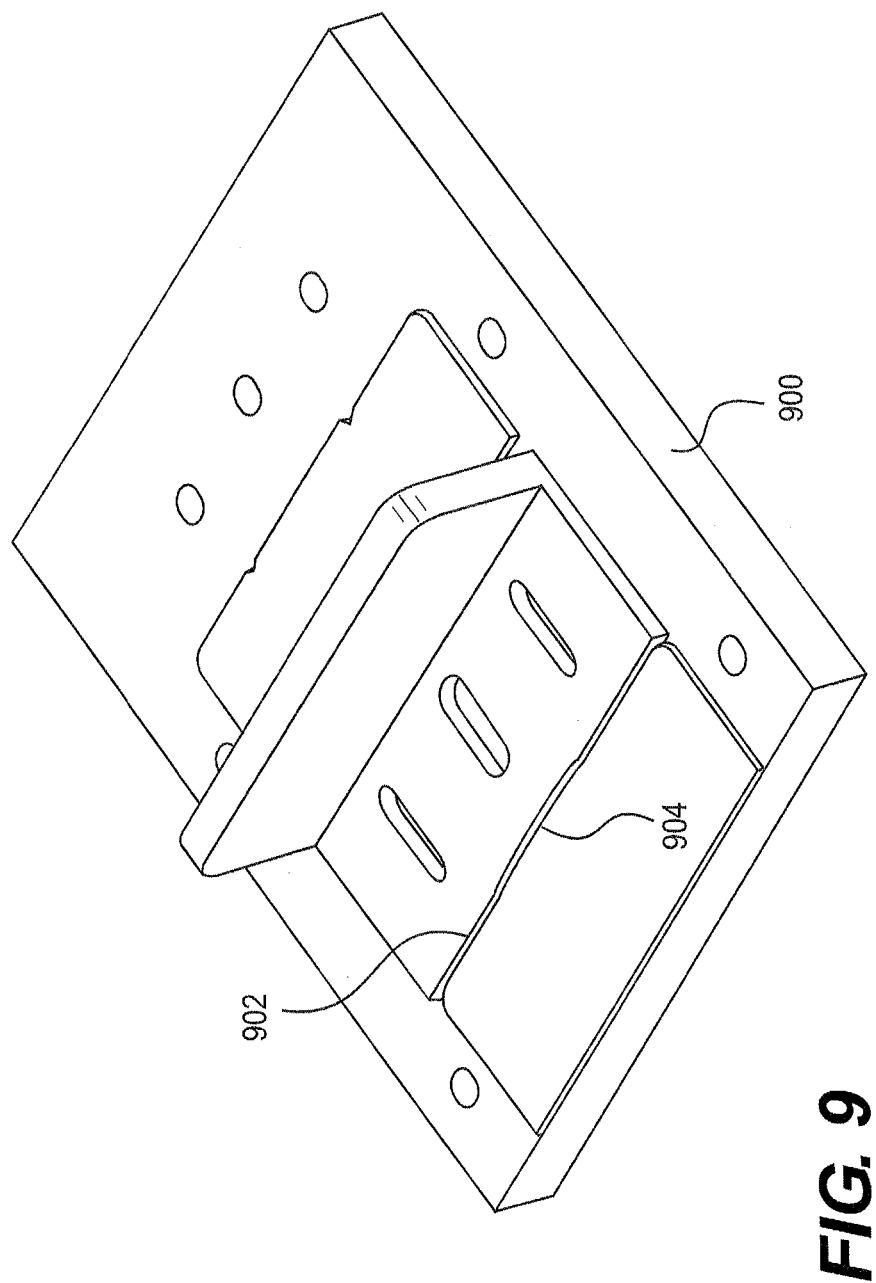
FIG. 9 depicts a fixture for molding a pre-shaped energy delivery electrode, consistent with embodiments of the present disclosure.

FIG. 9 depicts a fixture 900 for making an electrode wire consistent with the embodiments of the present disclosure, including the pre-shaped electrode wires of FIGS. 7A and 8A. Specifically, fixture 900 contains a plurality of contours 902 into which a wire may be disposed for deformation. Contours 902 may contain a concaved portion 904, which may impart a concaved feature, e.g., concave portion 702, onto an electrode wire. In one embodiment, a Nitinol ribbon, or other shape memory material, may be set into the contours 902 of fixture 900. A press plate may be used to press the Nitinol ribbon or other wire against the desired contours formed in the fixture 900. Heat may be applied to the wire to aid in deforming the wire against the contours 902 of fixture 900, thereby pre-setting the shape of the wire.

Figure 10:
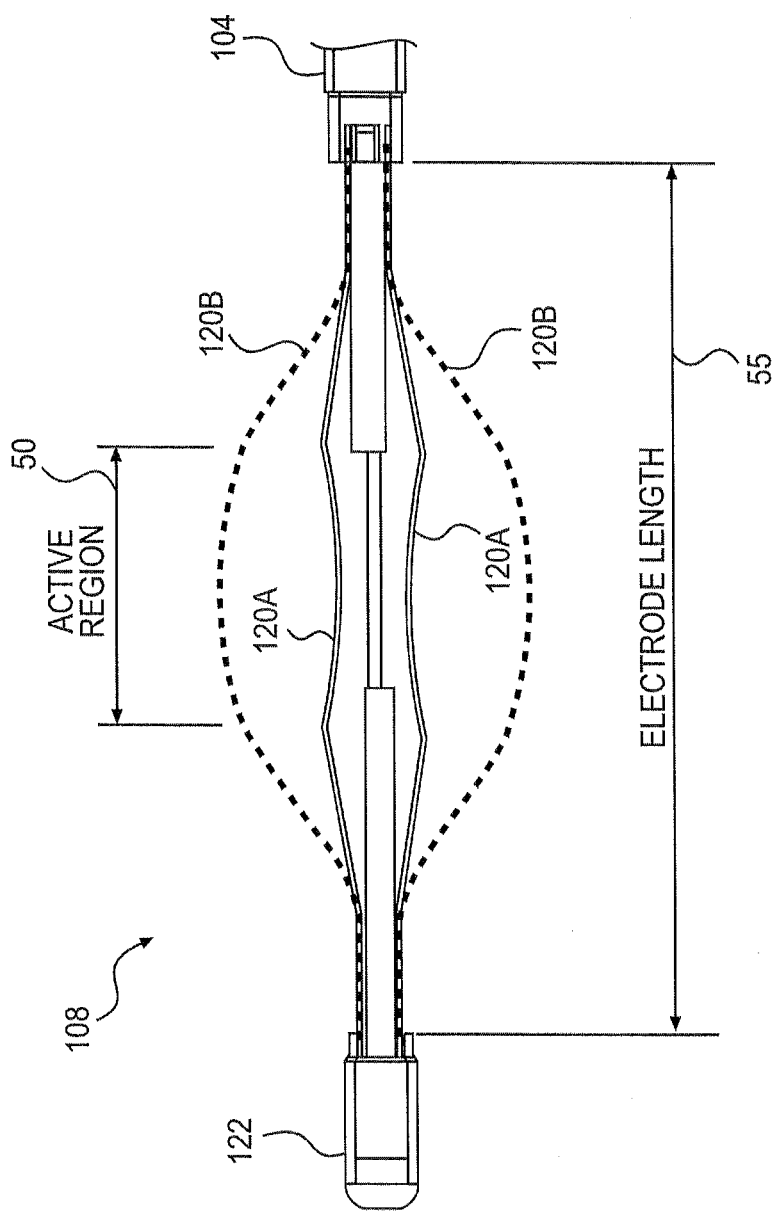
FIG. 10 depicts a cross-sectional diagram of an exemplary energy delivery device consistent with embodiments of the present disclosure.

FIG. 10 depicts an embodiment of energy delivery device 108 including electrode arms 120A/120B consistent with electrode arm 700/700' depicted in FIGS. 7A and 7B. FIG. 10 also depicts an embodiment of energy delivery element 108 including a representation of an active region 50. Specifically, the electrode arms of energy delivery element 108 may be originally shaped like electrode arms 120A, as shown in FIG. 10, when energy delivery element 108 is in a collapsed configuration. The electrode arms may be deformed to the shape of electrode arms 120B, by the application of axial compressive forces. Because the electrode arms 120A have concave portions consistent with concave portions 702 of FIG. 7A, a larger portion of active region 50 may be in contact with body lumen tissue, than of the active region depicted in FIG. 5. Moreover, contact area of the active region 50 of FIG. 10 may be a larger proportion of the active region 50 and/or of the overall electrode length 55, as compared to that of the electrode disclosed in FIG. 5.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A medical device for delivering energy to a body lumen, the device comprising:
an elongate member having a proximal end, a distal end, and a lumen extending therebetween; and
a basket assembly disposed at or adjacent the distal end and configured to transition between a collapsed state and an expanded state, wherein the basket assembly includes a plurality of expandable legs, wherein a first expandable leg of the plurality of expandable legs includes a first region disposed at or adjacent a proximal portion of the first expandable leg, a second region disposed distally of the first region, an active region disposed distally of the second region, a third region disposed distally of the active region, and a fourth region disposed distally of the third region, wherein the first expandable leg is pre-shaped such that in the collapsed state and while the basket assembly is unconstrained by an outer sheath:
the second region extends distally and radially outward from the first region,
the active region extends distally from (i) the second region in a radially inward curve toward a longitudinal axis of the medical device and toward a radially innermost point, and (ii) the radially innermost point in a radially outward curve toward the third region, and
the third region extends distally from the active region and radially inward toward the fourth region;
wherein the active region is configured to contact and deliver energy to the body lumen when the basket assembly is in the expanded state, and
when the basket assembly is in the expanded state, distal ends of the plurality of expandable legs converge toward one another.

2. The medical device of claim 1, wherein the active region includes an electrode secured to the first expandable leg.

3. The medical device of claim 1, wherein the active region of the first expandable leg exhibits a curvature when the basket assembly is in the collapsed state, and when the basket assembly is in the expanded state, the active region of the first expandable leg is substantially flat.

4. The medical device of claim 1, wherein portions of the first expandable leg proximal and distal to the active region include an insulating coating.

5. The medical device of claim 1, wherein the plurality of expandable legs are radially spaced from one another about the longitudinal axis of the medical device.

6. The medical device of claim 1, wherein the plurality of expandable legs are configured to deliver RF energy.

7. The medical device of claim 1, further including a distal tip, wherein the distal end of each of the plurality of expandable legs is coupled to the distal tip.

8. The medical device of claim 7, further including an actuating member that extends from the distal end of the elongate member, through a volume defined by the plurality of expandable legs, to the distal tip.

9. A medical device for delivering energy to a body lumen, the device comprising:
a flexible elongate member comprising a proximal portion and a distal portion; and
an energy delivery device disposed at or adjacent the distal portion of the elongate member, the energy delivery device comprising at a plurality of electrodes, the energy delivery device being configured to move between an expanded state and a collapsed state;
wherein at least one of the plurality of electrodes comprises a proximal adjoining region, an active region disposed distally of the proximal adjoining region, and a distal adjoining region disposed distally of the active region, wherein the active region is configured to contact and deliver energy to the body lumen when the energy delivery device is in the expanded state; and
wherein, when the energy delivery device is in the collapsed state and while the energy delivery device is unconstrained by an outer sheath, at least a portion of the active region of the at least one electrode is pre-shaped such that it bows radially inward toward a longitudinal axis of the energy delivery device from both the proximal adjoining region and the distal adjoining region, such that at least a portion of the active region is closer to the longitudinal axis than at least a portion of the proximal adjoining region and at least a portion of the distal adjoining region,
wherein, when the energy delivery device is in the expanded state, distal ends of the plurality of electrodes converge toward one another.

10. The medical device of claim 9, wherein the proximal adjoining region and the distal adjoining region are either substantially flat or bow radially inward toward the longitudinal axis of the energy delivery device.

11. The medical device of claim 9, wherein, when the energy delivery device is in the expanded state, the active region becomes substantially flat, and at least a portion of the active region becomes positioned farther from the longitudinal axis than at least the portion of the proximal adjoining region and at least the portion of the distal adjoining region.

12. The medical device of claim 9, wherein the plurality of electrodes form an expandable basket assembly.

13. The medical device of claim 1, wherein, when the basket assembly is in the collapsed state, the active region of the first expandable leg, is convex with respect to the longitudinal axis of the medical device.

14. The medical device of claim 1, wherein the first and fourth regions of the first expandable leg are substantially flat in both the collapsed state and the expanded state of the basket assembly.

15. The medical device of claim 9, wherein the active region of the at least one electrode is convex with respect to the longitudinal axis of the energy delivery device when the energy delivery device is in the collapsed state.

16. The medical device of claim 9, wherein the plurality of electrodes are radially spaced from one another about the longitudinal axis of the energy delivery device.

17. The medical device of claim 9, wherein the plurality of electrodes are configured to deliver RF energy.

18. The medical device of claim 9, further including a distal tip, wherein the distal end of each of the plurality of electrodes is coupled to the distal tip.

19. The medical device of claim 18, further including an actuating member that extends from the distal end of the flexible elongate member, through a volume defined by the plurality of electrodes, to the distal tip.

\* \* \* \* \*